US009212056B2

(12) United States Patent
Breen et al.

(10) Patent No.: US 9,212,056 B2
(45) Date of Patent: *Dec. 15, 2015

(54) NANOPARTICLE INCLUDING MULTI-FUNCTIONAL LIGAND AND METHOD

(75) Inventors: Craig Breen, Somerville, MA (US); John R. Linton, Concord, MA (US)

(73) Assignee: QD VISION, INC., Lexington, MA (US)

( * ) Notice: Subject to any disclaimer, the term of this patent is extended or adjusted under 35 U.S.C. 154(b) by 638 days.

This patent is subject to a terminal disclaimer.

(21) Appl. No.: 13/015,651

(22) Filed: Jan. 28, 2011

(65) Prior Publication Data

US 2011/0245533 A1    Oct. 6, 2011

Related U.S. Application Data

(63) Continuation of application No. PCT/US2009/004345, filed on Jul. 28, 2009, and a continuation-in-part of application No. 12/722,028, filed on Mar. 11, 2010, now Pat. No. 8,845,927, which is a continuation of application No. PCT/US2008/010651, filed on Sep. 12, 2008, which is a continuation-in-part of application No. PCT/US2007/013152, filed on Jun. 4, 2007.

(60) Provisional application No. 61/083,998, filed on Jul. 28, 2008, provisional application No. 61/140,051, filed on Dec. 22, 2008, provisional application No. 61/159,351, filed on Mar. 11, 2009, provisional application No. 60/971,887, filed on Sep. 12, 2007, provisional application No. 60/992,598, filed on Dec. 5, 2007, provisional application No. 60/971,885, filed on Sep. 12, 2007, provisional application No. 60/973,644, filed on Sep. 19, 2007, provisional application No. 61/016,227, filed on Dec. 21, 2007, provisional application No. 60/886,261, filed on Jan. 23, 2007, provisional application No. 60/825,370, filed on Sep. 12, 2006, provisional application No. 60/825,374, filed on Sep. 12, 2006, provisional application No. 60/825,373, filed on Sep. 12, 2006, provisional application No. 60/804,921, filed on Jun. 15, 2006, provisional application No. 60/810,914, filed on Jun. 5, 2006, provisional application No. 60/810,767, filed on Jun. 2, 2006.

(51) Int. Cl.
| | |
|---|---|
| *C07F 9/38* | (2006.01) |
| *C07F 9/00* | (2006.01) |
| *C01B 13/14* | (2006.01) |
| *H01B 1/12* | (2006.01) |
| *H01B 1/06* | (2006.01) |
| *B82Y 30/00* | (2011.01) |
| *C30B 29/60* | (2006.01) |
| *C30B 33/00* | (2006.01) |
| *G01N 33/543* | (2006.01) |
| *G01N 33/58* | (2006.01) |

(52) U.S. Cl.
CPC ............... *B82Y 30/00* (2013.01); *C30B 29/605* (2013.01); *C30B 33/00* (2013.01); *G01N 33/54346* (2013.01); *G01N 33/587* (2013.01)

(58) Field of Classification Search
CPC ............. C07F 9/38; C07F 9/00; C01B 13/14; H01B 1/12; H01B 1/06
USPC ............. 252/301.16, 519.2, 301.6 S, 301.6 P, 252/301.4 S, 301.4 P, 500; 257/103
See application file for complete search history.

(56) References Cited

U.S. PATENT DOCUMENTS

| | | |
|---|---|---|
| 4,789,753 A | 12/1988 | Billig et al. |
| 4,994,429 A | 2/1991 | Wieserman et al. |

(Continued)

FOREIGN PATENT DOCUMENTS

| | | | | |
|---|---|---|---|---|
| AU | A-54514/96 | 12/1995 | | |
| EP | 745646 A1 | * 12/1996 | ............... | C08K 9/12 |

(Continued)

OTHER PUBLICATIONS

CAS reg. No. 57877-93-7, Nov. 16, 1984.

(Continued)

Primary Examiner — Douglas M C Ginty

(57) ABSTRACT

A nanoparticle including an inorganic core comprising at least one metal and/or at least one semi-conductor compound comprising at least one metal includes a coating or shell disposed over at least a portion of a surface of the core. The coating can include one or more layers. Each layer of the coating can comprise a metal and/or at least one semiconductor compound. The nanoparticle further includes a ligand attached to a surface of the coating. The ligand is represented by the formula: X-Sp-Z, wherein: X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group; Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light. Compositions including a nanoparticle in accordance with the invention are also disclosed. Devices including nanoparticle and/or composition in accordance with the invention are disclosed. Methods for preparing nanoparticles in accordance with the invention are disclosed. Other products including a nanoparticle in accordance with the invention are also disclosed.

20 Claims, 3 Drawing Sheets

(56) References Cited

U.S. PATENT DOCUMENTS

| | | | |
|---|---|---|---|
| 5,064,718 A | 11/1991 | Buscall et al. | |
| 5,399,694 A | 3/1995 | Riess et al. | |
| 5,648,362 A | 7/1997 | Riess et al. | |
| 5,677,545 A * | 10/1997 | Shi et al. | 257/40 |
| 5,751,018 A | 5/1998 | Alivisatos et al. | |
| 5,981,467 A | 11/1999 | Hogan, Jr. | |
| 6,069,442 A | 5/2000 | Hung et al. | |
| 6,114,038 A | 9/2000 | Castro et al. | |
| 6,207,229 B1 | 3/2001 | Bawendi et al. | |
| 6,235,540 B1 | 5/2001 | Siiman et al. | |
| 6,251,303 B1 | 6/2001 | Bawendi et al. | |
| 6,306,610 B1 | 10/2001 | Bawendi et al. | |
| 6,319,426 B1 * | 11/2001 | Bawendi et al. | 252/301.4 R |
| 6,319,607 B1 | 11/2001 | Barbera-Gullium et al. | |
| 6,322,901 B1 | 11/2001 | Bawendi et al. | |
| 6,444,143 B2 | 9/2002 | Bawendi et al. | |
| 6,468,808 B1 | 10/2002 | Nie et al. | |
| 6,473,554 B1 | 10/2002 | Pelka et al. | |
| 6,548,168 B1 | 4/2003 | Mulvaney et al. | |
| 6,563,186 B2 | 5/2003 | Liu et al. | |
| 6,714,711 B1 | 3/2004 | Lieberman et al. | |
| 6,797,412 B1 | 9/2004 | Jain et al. | |
| 6,801,270 B2 | 10/2004 | Faris et al. | |
| 6,805,922 B2 | 10/2004 | Heeney et al. | |
| 6,855,202 B2 | 2/2005 | Alivisatos et al. | |
| 6,869,545 B2 * | 3/2005 | Peng et al. | 252/301.6 S |
| 6,887,517 B1 | 5/2005 | Cook et al. | |
| 6,949,206 B2 * | 9/2005 | Whiteford et al. | 252/500 |
| 7,041,362 B2 | 5/2006 | Barbera-Guillem | |
| 7,065,285 B2 | 6/2006 | Chen et al. | |
| 7,108,915 B2 | 9/2006 | Adams et al. | |
| 7,147,917 B2 | 12/2006 | Adams et al. | |
| 7,160,613 B2 * | 1/2007 | Bawendi et al. | 428/403 |
| 7,190,870 B2 | 3/2007 | Sundar et al. | |
| 7,198,847 B2 | 4/2007 | Naasani | |
| 7,199,393 B2 | 4/2007 | Park et al. | |
| 7,214,428 B2 | 5/2007 | Naasani | |
| 7,244,498 B2 | 7/2007 | Cook et al. | |
| 7,250,082 B2 | 7/2007 | Jang et al. | |
| 7,253,452 B2 * | 8/2007 | Steckel et al. | 257/103 |
| 7,267,875 B2 | 9/2007 | Whiteford et al. | |
| 7,309,525 B2 | 12/2007 | Reiss et al. | |
| 7,311,774 B2 | 12/2007 | Alivisatos et al. | |
| 7,329,369 B2 | 2/2008 | Sato et al. | |
| 7,335,418 B2 | 2/2008 | Sato et al. | |
| 7,361,516 B2 | 4/2008 | Uyeda et al. | |
| 7,364,919 B2 | 4/2008 | Penades et al. | |
| 7,368,086 B2 | 5/2008 | Naasani | |
| 7,374,807 B2 * | 5/2008 | Parce et al. | 428/76 |
| 7,387,833 B2 | 6/2008 | Reiss et al. | |
| 7,416,784 B2 | 8/2008 | Mitsunaga et al. | |
| 7,422,790 B1 | 9/2008 | Scher et al. | |
| 7,459,145 B2 | 12/2008 | Bao et al. | |
| 7,488,819 B2 | 2/2009 | Manabe et al. | |
| 7,589,240 B2 | 9/2009 | Emrick et al. | |
| 7,662,313 B2 | 2/2010 | Whiteford et al. | |
| 7,989,153 B2 | 8/2011 | Skipor et al. | |
| 8,718,437 B2 | 5/2014 | Coe-Sullivan et al. | |
| 8,845,927 B2 * | 9/2014 | Breen et al. | 252/301.4 P |
| 8,849,087 B2 | 9/2014 | Breen et al. | |
| 2002/0016306 A1 | 2/2002 | Hutchinson et al. | |
| 2002/0020830 A1 | 2/2002 | Bass et al. | |
| 2002/0146590 A1 | 10/2002 | Matsuo et al. | |
| 2003/0042850 A1 | 3/2003 | Bertram et al. | |
| 2003/0059635 A1 * | 3/2003 | Naasani | 428/473.5 |
| 2003/0091933 A1 | 5/2003 | Kunita | |
| 2004/0023010 A1 * | 2/2004 | Bulovic et al. | 428/209 |
| 2004/0023261 A1 * | 2/2004 | Bruchez et al. | 435/6 |
| 2004/0048241 A1 * | 3/2004 | Freeman et al. | 435/5 |
| 2004/0105980 A1 | 6/2004 | Sudarshan et al. | |
| 2004/0110002 A1 | 6/2004 | Kim et al. | |
| 2004/0137263 A1 | 7/2004 | Burn et al. | |
| 2004/0146560 A1 | 7/2004 | Whiteford et al. | |
| 2004/0265571 A1 * | 12/2004 | Schwartz et al. | 428/333 |
| 2005/0058416 A1 | 3/2005 | Lee et al. | |
| 2005/0129947 A1 * | 6/2005 | Peng et al. | 428/403 |
| 2005/0214536 A1 | 9/2005 | Schrier et al. | |
| 2005/0258418 A1 * | 11/2005 | Steckel et al. | 257/40 |
| 2005/0265922 A1 | 12/2005 | Nie et al. | |
| 2005/0266246 A1 * | 12/2005 | Reiss et al. | 428/403 |
| 2006/0040103 A1 | 2/2006 | Whiteford et al. | |
| 2006/0042685 A1 | 3/2006 | Wang | |
| 2006/0068506 A1 | 3/2006 | Uyeda et al. | |
| 2006/0083694 A1 | 4/2006 | Kodas et al. | |
| 2006/0128845 A1 * | 6/2006 | Emrick et al. | 524/115 |
| 2006/0130741 A1 | 6/2006 | Peng et al. | |
| 2006/0216508 A1 * | 9/2006 | Denisyuk et al. | 428/402 |
| 2006/0216510 A1 * | 9/2006 | Denisyuk et al. | 428/403 |
| 2006/0216759 A1 | 9/2006 | Naasani et al. | |
| 2006/0270233 A1 | 11/2006 | Xia et al. | |
| 2007/0034833 A1 | 2/2007 | Parce et al. | |
| 2007/0036962 A1 | 2/2007 | Sasaki et al. | |
| 2007/0072979 A1 | 3/2007 | Moad et al. | |
| 2007/0103068 A1 * | 5/2007 | Bawendi et al. | 313/506 |
| 2007/0131905 A1 | 6/2007 | Sato et al. | |
| 2007/0269904 A1 | 11/2007 | Uyeda et al. | |
| 2008/0001167 A1 * | 1/2008 | Coe-Sullivan et al. | 257/146 |
| 2008/0038361 A1 | 2/2008 | Cheon et al. | |
| 2008/0085088 A1 | 4/2008 | Lin et al. | |
| 2008/0089836 A1 | 4/2008 | Hainfeld | |
| 2008/0103219 A1 | 5/2008 | Petruska et al. | |
| 2008/0144333 A1 | 6/2008 | Gourlay | |
| 2009/0152567 A1 * | 6/2009 | Comerford et al. | 257/80 |
| 2009/0162011 A1 | 6/2009 | Coe-Sullivan et al. | 385/31 |
| 2009/0181478 A1 * | 7/2009 | Cox et al. | 438/22 |
| 2009/0215208 A1 * | 8/2009 | Coe-Sullivan et al. | 438/22 |
| 2009/0215209 A1 * | 8/2009 | Anc et al. | 438/22 |
| 2009/0251759 A1 * | 10/2009 | Domash et al. | 359/288 |
| 2009/0278141 A1 * | 11/2009 | Coe-Sullivan et al. | 257/89 |
| 2009/0280586 A1 | 11/2009 | Coe-Sullivan | |
| 2009/0283743 A1 * | 11/2009 | Coe-Sullivan et al. | 257/9 |
| 2009/0283778 A1 * | 11/2009 | Coe-Sullivan et al. | 257/88 |
| 2010/0001256 A1 * | 1/2010 | Coe-Sullivan et al. | 257/13 |
| 2010/0027192 A1 | 2/2010 | Perry et al. | |
| 2010/0044635 A1 * | 2/2010 | Breen et al. | 252/301.6 S |
| 2010/0044636 A1 * | 2/2010 | Ramprasad et al. | 252/301.6 S |
| 2010/0051870 A1 * | 3/2010 | Ramprasad | 252/301.33 |
| 2010/0051901 A1 * | 3/2010 | Kazlas et al. | 257/13 |
| 2010/0051917 A1 | 3/2010 | Kippelen et al. | |
| 2010/0052512 A1 * | 3/2010 | Clough et al. | 313/498 |
| 2010/0068468 A1 * | 3/2010 | Coe-Sullivan et al. | 428/172 |
| 2010/0132770 A1 | 6/2010 | Beatty et al. | 136/252 |
| 2010/0265307 A1 * | 10/2010 | Linton et al. | 347/100 |
| 2010/0283014 A1 * | 11/2010 | Breen et al. | 252/519.2 |
| 2010/0314646 A1 * | 12/2010 | Breen et al. | 257/98 |
| 2011/0049442 A1 | 3/2011 | Schreuder et al. | |
| 2011/0103064 A1 | 5/2011 | Coe-Sullivan | |
| 2011/0140075 A1 | 6/2011 | Zhou et al. | |
| 2011/0186811 A1 | 8/2011 | Coe-Sullivan et al. | |
| 2011/0223425 A1 | 9/2011 | Schreuder et al. | |
| 2011/0233483 A1 * | 9/2011 | Breen et al. | 252/519.2 |
| 2011/0245533 A1 | 10/2011 | Breen et al. | |
| 2011/0256404 A1 | 10/2011 | Tulsky et al. | |
| 2015/0086169 A1 * | 3/2015 | Breen et al. | 385/131 |

FOREIGN PATENT DOCUMENTS

| | | | | |
|---|---|---|---|---|
| JP | 2002053319 A | 2/2002 | | |
| JP | 2002079076 A | 3/2002 | | |
| WO | WO-2007001438 A2 | 3/2002 | | |
| WO | WO-2006088877 A1 | 8/2006 | | |
| WO | WO-2007143197 A2 | 12/2007 | | |
| WO | WO-2008070028 A2 | 6/2008 | | |
| WO | WO-2009002512 A1 | 12/2008 | | |
| WO | WO 2009035657 A1 * | 3/2009 | A61K 49/00 | |
| WO | WO-2009035657 A1 | 3/2009 | | |
| WO | WO 2009145813 A1 * | 12/2009 | C30B 7/08 | |
| WO | WO-2010039897 A2 | 4/2010 | | |

OTHER PUBLICATIONS

Coe-Sullivan, et al., "Large-Area Ordered Quantum-Dot Monolayers via Phase Separation During Spin-Casting", *Adv. Func. Mater.*, (2005), vol. 15, pp. 1117-1124.

(56) References Cited

OTHER PUBLICATIONS

Dabbousi, et al., "(CdSe) ZnS Core-Shell Quantum Dots: Synthesis and Characterizaqtion of a Size Series of Highly Luminescent Nanocrystallites", *J. Phys. Chem.* 101, 9463, 1997.

de Mello et al., "An Improved Experimental Determination of External Photoluminescence Quantum Efficiency", *Advanced Materials* 9 (3) pp. 230-232 (1997).

Diamente, et al., "Bioconjugation of $Ln^{3+}$-Doped $LaF_3$ Nanoparticles to Avidin", *Langmuir*, (2006), 22, 1782-1788.

Doussineau, et al., "Synthesis of Phosphonic Acids with the Semicarbazide Group for the Functionalization of Metal Oxide and Zeolite Nanoparticles", *Synlett* (2004), No. 10, pp. 1735-1738.

EPO Communication under rule 71(3) mailed Sep. 20, 2013, in European Patent Application No. 08 831 106.3, which is the European counterpart of U.S. Appl. No. 12/722,028 now U.S. Patent. No. 8,845,927.

European Counterpart EP Application No. 08 831 106.3-1223—Extended European Search Report dated Jan. 13, 2011 which is the European counterpart of U.S. Appl. No. 12/722,028 now U.S. Patent No. 8,845,927.

European Counterpart EP Application No. 08 831 106.3-1223 Communication dated Sep. 22, 2011 which is the European counterpart of U.S. Appl. No. 12/722,028 now U.S. Patent No. 8,845,927.

Final Office Action, mailed May 1, 2014, in copending U.S. Appl. No. 13/015,670, filed Jan. 28, 2011.

Ichikawa, et al., "Bipyridyl oxadiazoles as efficient and durable electron-transporting and hole-blocking molecular materials", *J. Mater. Chem.*, (2006), vol. 16, pp. 221-225.

Japanese Office Action mailed Aug. 27, 2013, in Japanese Patent Application No. 2010-524868 which is the Japanese counterpart of U.S. Appl. No. 12/722,028 now U.S. Patent No. 8,845,927.

Kazlas, et al., "Progress in Developing High Efficiency Quantum Dot Displays", *SID Symposium Digest of Technical Papers*—May 2007, vol. 38, Issue 1, pp. 856-859.

Kopping, et al., "Identification of Acidic Phosphorus-Containing Ligands Involved in the Surface Chemistry of CdSe Nanoparticles Prepared in Tri-*N*-octylphosphine Oxide Solvents", *J. Am. Chem. Soc.*, Published on web: Apr. 5, 2008.

Kopping, et al., Supporting Information for: "Identification of Acidic Phosphorus-Containing Ligands Involved in the Surface Chemistry of CdSe Nanoparticles Prepared in Tri-*N*-octylphosphine Oxide Solvents" *J. Am. Chem. Soc.*, Department of Chemistry, U of Cal at Davis, 2008.

Lorenz, et al., "Surfactant—Semiconductor Interfaces: Perturbation of the Photoluminescence of Bulk Cadmium Selenide by Adsorption of Tri-*n*-octylphosphine Oxide as a Probe of Solution Aggregation v Relevance to Nanocrystal Stabilization", *J. Am Chem. Soc.* 1998, 120, 10970-10975.

Murase, et al., "Ligand Control of Semiconductor Nanocrystals for Efficient Carrier Injection", *Mater. Res. Soc. Symp. Proc* (2005), vol. 847, EE13.25.1-EE13.25.5.

Murray, C. B., et al., "Synthesis and Characterization of Monodisperse Nanocrystalls and Close-Packed Nanocrystal Assemblies", *Annu. Rev. Mater. Sci.* 2000, 30, 545.

Murray, et al., "Synthesis and Characterization of Nearly Monodisperse CdE (E=S, Se, Te) Semiconductor Nanocrystallites", *J. Am. Chem. Soc.*, 115:8706 (1993).

Nonfinal Office Action, mailed Nov. 7, 2013, in copending U.S. Appl. No. 13/015,670, filed Jan. 28, 2011.

Nonfinal Office Action, mailed Oct. 14, 2014, in copending U.S. Appl. No. 13/015,670, filed Jan. 28, 2011.

PCT/US2007/13152 Search Report and Written Opinion—QD Vision, Inc., mailed Jul. 18, 2008.

PCT/US2007/24750 Search Report and Written Opinion—QD Vision, Inc., mailed Apr. 22, 2008.

PCT/US2008/10651 Search Report and Written Opinion—QD Vision, Inc., mailed Dec. 5, 2008.

PCT/US2009/04345 Search Report and Written Opinion—QD Vision, Inc., mailed Oct. 5, 2009.

PCT/US2009/04354 Search Report and Written Opinion—QD Vision, Inc., mailed Oct. 23, 2009.

Puzder, et al., "The Effect of Organic Ligand Binding on the Growth CdSe Nanoparticles Probed by Ab-Initio Calculations", Nanoletters (2004), Oct. 27, pp. 1-6.

Schreuder, et al., "Control of Surface State Emission via Phosphonic Acid Modulation in Ultrasmall CdSe Nanocrystals: The Role of Ligand Electronegativity", J. Phys. Chem. C (2009), vol. 113 (19), pp. 8169-8176.

Shandryuk, et al, "Effect of H-Bonded Liquid Crystal Polymers on CdSe Quantum Dot Alignment within Nanocomposite", *Macromolecules*(2008), vol. 41, pp. 2178-2185.

Steckel, Jonathan S., Thesis entitled "The Synthesis of Inorganic Semiconductor Nanocrystalline Materials for the Purpose of Creating Hybrid Organic/Inorganic Light-Emitting Devices", Massachusetts Institute of Technology, Sep. 2006.

Steigerwald, et al., "Synthesis, Stabilization, and Electronic Structure of Quantum Semiconductor Nanoclusters",*Annu. Mater. Sci.* (1989), vol. 19, pp. 471-495.

Talapin, et al., "Highly Luminescent Monodisperse CdSe and CdSe/ZnS Nanocrystals Synthesized in a Hexadecylamine—Trioctylphosphine Oxide—Trioctylphospine Mixture", *Nano Letters* (2001), vol. 1, No. 4 207-211.

Van Embden, et al., "Nucleation and Growth of CdSe Nanocrystals in a Binary Ligand System", *Langmuir* (2005), vol. 21, pp. 10226-10233.

Wang, et al., Supporting Information for: "Trouble with TOPO; Identification of Adventitious Impurities Beneficial to the Growth of Cadmium Selenide Quantum Dots, Rods, and Wires", *Department of Chemistry and Center for Materials Innovation*, Washington Univ., Saint Louis, MS—2008.

Wang, et al., Nano Letters, "Trouble with TOPO; Identification of Adventitious Impurities Beneficial to the Growth of Cadmium Selenide Quantum Dots, Rods, and Wires", Printed on web: Aug. 29, 2008.

\* cited by examiner

NANOPARTICLE INCLUDING MULTI-FUNCTIONAL LIGAND AND METHOD

This application is a continuation of commonly owned International Application No. PCT/US2009/004345 filed 28 Jul. 2009, which was published in the English language as PCT Publication No. WO 2010/14198 on 4 Feb. 2010, which International Application claims priority to U.S. patent application No. 61/083,998 filed 28 Jul. 2008, 61/140,051 filed 22 Dec. 2008, and 61/159,351 filed 11 Mar. 2009, and International Application No. PCT/US2008/010651 filed 12 Sep. 2008. Each of the foregoing applications is hereby incorporated herein by reference in its entirety.

This application is also a continuation-in-part of commonly owned U.S. application Ser. No. 12/722,028, filed 11 Mar. 2010, now U.S. Pat. No. 8,845,927, which is a continuation of International Application No. PCT/US2008/010651 filed 12 Sep. 2008, which International Application claims priority to U.S. Application Nos. 60/971,887, filed 12 Sep. 2007; 60/992,598, filed 5 Dec. 2007; 61/083,998, filed 28 Jul. 2008, 60/971,885, filed 12 Sep. 2007; 60/973,644, filed 19 Sep. 2007; and 61/016,227, filed 21 Dec. 2007, International Application No. PCT/US2007/024750, filed 3 Dec. 2007, and International Application No. PCT/US2008/007902, filed 25 Jun. 2008. International Application No. PCT/US2008/010651 is also a continuation-in-part application of International Application No. PCT/US2007/013152, filed 4 Jun. 2007, which claims priority from U.S. Patent Application Nos. 60/810,767 filed 2 Jun. 2006, 60/810,914 filed 5 Jun. 2006, 60/804,921 filed 15 Jun. 2006, 60/825,373 filed 12 Sep. 2006, 60/825,374 filed 12 Sep. 2006, 60/825,370 filed 12 Sep. 2006, and 60/886,261 filed 23 Jan. 2007.

TECHNICAL FIELD

The present invention relates to the technical field of nanoparticles and more particularly nanoparticles including ligands, compositions, devices, and other products including same, and related methods.

SUMMARY OF THE INVENTION

The present invention relates to nanoparticles including one or more ligands attached to a surface of the nanoparticle. The present invention further relates to compositions including such nanoparticles. The present invention further relates to devices including such nanoparticles. The present invention further relates to devices including such compositions. The present invention also relates to methods for preparing a nanoparticle in the presence of one or more ligands.

In accordance with one aspect of the present invention, there is provided a nanoparticle including a ligand attached to a surface thereof, wherein the ligand is represented by the formula:

X-Sp-Z wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light.

In certain embodiments, Z represents a multifunctional group including a first functional group having at least two functional substituent groups attached thereto, the multifunctional group being capable of communicating a specific property or chemical reactivity to the nanoparticle. In certain of such embodiments, at least two of the two or more functional substituent groups are chemically distinct from each other. In certain of such embodiments, the first functional group and at least two or the functional substituent groups are chemically distinct from each other.

In certain embodiments, Z includes one or more functional groups that exhibit dispersion bonding characteristics, polar bonding characteristics, and/or hydrogen bonding characteristics.

In certain embodiments, Z includes one or more functional groups that impart predetermined chemical miscibility properties to the nanoparticle to which it is attached.

In certain embodiments, Z includes one or more functional groups that exhibit polar, a halogen, aliphatic, and/or aromatic character.

Examples of functional groups that exhibit polar character include, but are not limited to, protic species such as hydroxyl, amino, carboxyl, etc. or polar a-protic species such as alkoxy, esters, amides, imides, nitriles, nitroso, etc.

In certain embodiments, a halogenated functional group can be incorporated into a ligand by including a halogen substituent (e.g., F, Cl, Br, and I).

In certain embodiments, an aromatic functional group includes, but not limited to phenyl, benzyl, naphthyl, biphenyl, fluorenyl, triarylamine, etc.

In certain embodiments, Z includes an heterocyclic ring, an aryl group, an aryl group condensed on one or several other aryl rings and/or alkyl and/or heterocyclic rings, a cycloalkyl group, a cycloalkyl alkyl group, an alkyl-cycloalkyl group, an arylalkyl group, an alkylaryl group, a heterocycloalkyl group or a alkyl-heterocycloalkyl group, wherein the group or ring includes one, two, or more functional groups attached thereto. In certain embodiments, a cycloalkyl group can be unsaturated and non-aromatic.

In certain embodiments, Z includes one or more aliphatic functional groups. An aliphatic group comprises a saturated hydrocarbon or unsaturated hydrocarbon group that can optionally be further substituted or functionalized. In certain embodiments, an aliphatic group includes, for example, but not limited to $C_{1-20}$ hydrocarbon. In certain embodiments, an aliphatic group comprises a $C_1$-$C_{20}$ hydrocarbon chain. In certain embodiments, an aliphatic group comprises a $C_2$-$C_{20}$ hydrocarbon. In certain embodiments, an aliphatic group is straight. In certain embodiments, an aliphatic group is branched, e.g., t-butyl, ethyl hexyl, etc. In certain embodiments, an aliphatic group can include at least one hetero-atom. In certain embodiments, an aliphatic group comprises a $C_1$-$C_{20}$ alkyl hydrocarbon. In certain embodiments, the aliphatic group comprises a $C_2$-$C_{20}$ alkyl hydrocarbon. In certain embodiments, an alkyl group is branched. In certain embodiments, an alkyl group is straight. In certain embodiments, an alkyl group can include at least one hetero-atom.

In certain embodiments, a functional group can comprise an organic group (e.g., including, but not limited to, an aromatic or an aliphatic (a saturated or unsaturated non-aromatic, cyclic or non-cyclic) group that includes two or more functional substituent groups attached thereto.

In certain embodiments, Z includes an alkyl group including two or more functional substituent groups. In certain embodiments, the alkyl group is branched. In certain embodiments, the alkyl group is straight. In certain embodiments, the alkyl group comprises a $C_1$-$C_{20}$ hydrocarbon. In certain embodiments, the alkyl group comprises a $C_2$-$C_{20}$ hydrocarbon. In certain embodiments, an alkyl group can include at least one hetero-atom.

In certain embodiments, Z includes a cyclic group including two or more functional groups. In certain embodiments, a cyclic group can comprise a saturated or unsaturated cyclic (including, but not limited to, a single ring, a bicyclic structure, a multi-cyclic structure, etc.) compound or aromatic compound. In certain embodiments, a cyclic group can include at least one hetero-atom.

In certain embodiments, a functional group can comprise a thiol, carboxyl, hydroxyl, amino, amine, sulfo, bifunctional group, polyfunctional group, etc.

In certain embodiments, a functional group can comprise a halogenated group (e.g., a fluorinated group, a perfluorinated group, a chlorinated group, a perchlorinated group, a brominated group, a perbrominated group, an iodinated group, a periodinated group, etc.) Other examples of halogenated groups can also be used.

In certain embodiments, a functional group can comprise a polar a-protic group. Examples of polar a-protic groups include, but are not limited to, a ketone, aldehyde, alkoxy, ester, amide, urea, urethane, or an imine. Other examples of polar a-protic groups are provided herein.

In certain embodiments, at least one functional group included in Z is selected to facilitate a colloidal dispersion of the nanoparticle in a specific solvent defined by a given polarity.

In certain embodiments, at least one of the functional groups included in Z is selected to facilitate colloidal dispersion of a plurality of nanoparticles in an a-polar solvent, non-polar, and/or a low polarity solvent. In certain embodiments, a low polarity solvent comprises a hydrocarbon.

In certain embodiments, at least one functional group included in Z is selected from among hydrophobic groups. In certain embodiments, Z is selected to not render the nanoparticle dispersible in a liquid medium that includes water.

In certain embodiments, at least one functional group included in Z is selected from among hydrophilic groups. In certain embodiments, Z is selected to render the nanoparticle dispersible in a liquid medium that includes water.

In certain embodiments, two or more identical or different Z groups are present on the same ligand.

In certain embodiments, the ligand is a native ligand.

In certain embodiments, one or more additional chemically distinct ligands can be attached to a surface of the nanoparticle.

In certain embodiments, the nanoparticle is water insoluble

In certain embodiments, the nanoparticle is overcoated to generate a core/shell or core/multi-shell nanoparticle in the presence of the ligand described above.

In certain embodiments, Z includes a heterocyclic ring, an aryl group, an aryl group condensed on one or several other aryl rings and/or alkyl and/or heterocyclic rings, a cycloalkyl group, a cycloalkyl alkyl group, an alkyl-cycloalkyl group, an arylalkyl group, an alkylaryl group, a heterocycloalkyl group or a alkyl-heterocycloalkyl group, wherein the group or ring includes two, or more chemically distinct functional groups attached thereto.

In certain embodiments, a nanoparticle includes two or more chemically distinct ligands attached to a surface thereof, wherein at least two of said ligands are represented by the formula:

X-Sp-Z.

X, Sp, and Z are as described herein.

In certain embodiments in which two or more chemically distinct ligands represented by the formula X-Sp-Z are attached to the nanoparticle, the X groups of at least two of said ligands are not the same.

In certain embodiments in which two or more chemically distinct ligands represented by the formula X-Sp-Z are attached to the nanoparticle, the Z groups of at least two of said ligands are not the same.

In certain embodiments in which two or more chemically distinct ligands represented by the formula X-Sp-Z are attached to the nanoparticle, the Sp groups of at least two of said ligands are not the same.

In certain embodiments, one or both of such ligands comprise a native ligand.

In certain embodiments, in which two or more chemically distinct ligands represented by the formula X-Sp-Z are attached to the nanoparticle, a first ligand can be represented by the formula:

N-Sp-Z wherein N represents a primary amine group, a secondary amine group, an imidizole group, an amide group; and a second ligand can be represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group.

In such embodiments, Sp, and Z are as described herein, and wherein each of Sp and Z on the first ligand and on the second ligand can independently be the same or different.

In certain embodiments, the nanoparticle exhibits photoluminescent properties.

In certain embodiments, the nanoparticle comprises a semiconductor material. In certain embodiments, the nanoparticle comprises a semiconductor nanocrystal.

In certain embodiments, the nanoparticle comprises a core comprising a first material and a shell disposed over at least a portion of a surface of the core, the shell comprising a second material.

In certain embodiments, the first material comprises a semiconductor material.

In certain embodiments, the second material comprises a semiconductor material.

In certain embodiments, one or more additional shells are disposed over at least a portion of a surface of the shell.

In certain embodiments, the semiconductor nanocrystal comprises a core comprising a first material and a shell disposed over at least a portion of a surface of the core, the shell comprising a second material.

In certain embodiments, the ligand represented by the formula X-Sp-Z comprises benzylphosphonic acid including at least two functional groups on the ring of the benzyl group (in addition to the Sp group attached thereto), a conjugate base thereof, or a mixture including one the foregoing.

In certain embodiments, the ligand represented by the formula X-Sp-Z comprises 3,5-di-tert-butyl-4-hydroxybenzylphosphonic acid, a conjugate base of the acid, or a mixture including one or more of the foregoing. The chemical structure of 3,5-di-tert-butyl-4-hydroxybenzylphosphonic acid is shown in FIG. 1. FIG. 3 provides a schematic diagram of 3,5-di-tert-butyl-4-hydroxybenzylphosphonic acid. This FIG. 3 is provided for illustrative purposes only and is not to be construed as a limitation on the scope of the invention.

In accordance with another aspect of the present invention there is provided a method for preparing the nanoparticle taught herein. The method comprises reacting precursors for forming a nanoparticle having a predetermined composition in the presence of a ligand represented by the formula:

X-Sp-Z, wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light.

In certain embodiments, Z represents a multifunctional group including a first functional group having at least two functional substituent groups attached thereto, the multifunctional group being capable of communicating a specific property or chemical reactivity to the nanoparticle. In certain of such embodiments, at least two of the two or more functional substituent groups are chemically distinct from each other. In certain of such embodiments, the first functional group and at least two or the functional substituent groups are chemically distinct from each other.

Examples of X, Sp, and Z include, but are not limited to, those described above and elsewhere herein.

In certain embodiments, the precursors include one or more metal-containing precursors and one or more chalcogen-containing or pnictogen-containing precursors.

In certain embodiments, the reaction is carried out in a liquid medium.

In certain embodiments, the liquid medium comprises a coordinating solvent.

In certain embodiments, the liquid medium comprises a non-coordinating solvent.

In certain embodiments, the mole ratio of total metal included in the one or more metal-containing precursors to total moles of ligand represented by the formula X-Sp-Z is in the range from about 1:0.1 to about 1:100.

In certain embodiments, the mole ratio of total moles of metal included in the one or more metal-containing precursors to total moles of ligand represented by the formula X-Sp-Z is in the range from about 1:1 to about 1:50.

In certain embodiments, the mole ratio of total moles of metal included in the one or more metal-containing precursors to total moles of ligand represented by the formula X-Sp-Z is in the range from about 1:1 to about 1:30.

In certain embodiments, the mole ratio of total moles of the liquid medium to total moles of ligand represented by the formula X-Sp-Z is in the range from about 500:1 to about 2:1.

In certain embodiments, the mole ratio of total moles of the liquid medium to total moles of ligand represented by the formula X-Sp-Z is in the range from about 100:1 to about 5:1.

In certain embodiments, the mole ratio of total moles of the liquid medium to total moles of ligand represented by the formula X-Sp-Z is in the range from about 50:1 to about 5:1.

In certain embodiments, the ligand represented by the formula X-Sp-Z comprises 3, 5-di-tert-butyl-4-hydroxybenzylphosphonic acid, a conjugate base of the acid, or a mixture including one or more of the foregoing.

In certain embodiments, the precursors are reacted in the presence of two or more chemically distinct ligands represented by the formula:

X-Sp-Z.

X, Sp, and Z are as described herein.

In certain embodiments, the precursors are reacted in the presence of two or more chemically distinct ligands wherein a first ligand is represented by the formula:

N-Sp-Z wherein N represents a primary amine group, a secondary amine group, an imidizole group, an amide group; and a second ligand is represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group.

In such embodiments, Sp, and Z are as described herein, and wherein each of Sp and Z on the first ligand and on the second ligand can independently be the same or different.

In accordance with another aspect of the present invention, there is provided a method for overcoating at least a portion of a surface of a nanoparticle with a coating material having a predetermined composition, the method comprising reacting precursors for the predetermined composition in the presence of a ligand represented by the formula:

X-Sp-Z wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light.

Examples of X, Sp, and Z include, but are not limited to, those described above and elsewhere herein.

In certain embodiments, the precursors include one or more metal-containing precursors and one or more chalcogen-containing or pnictogen-containing precursors.

In certain embodiments, the reaction is carried out in a liquid medium.

In certain embodiments, the liquid medium comprises a coordinating solvent.

In certain embodiments, the liquid medium comprises a non-coordinating solvent.

In certain embodiments, the mole ratio of total metal included in the one or more metal-containing precursors to total moles of ligand represented by the formula X-Sp-Z is in the range from about 1:0.1 to about 1:100.

In certain embodiments, the mole ratio of total moles of metal included in the one or more metal-containing precursors to total moles of ligand represented by the formula X-Sp-Z is in the range from about 1:1 to about 1:50.

In certain embodiments, the mole ratio of total moles of metal included in the one or more metal-containing precursors to total moles of ligand represented by the formula X-Sp-Z is in the range from about 1:1 to about 1:30.

In certain embodiments, the mole ratio of total moles of the liquid medium to total moles of ligand represented by the formula X-Sp-Z is in the range from about 500:1 to about 2:1.

In certain embodiments, the mole ratio of total moles of the liquid medium to total moles of ligand represented by the formula X-Sp-Z is in the range from about 100:1 to about 5:1.

In certain embodiments, the mole ratio of total moles of the liquid medium to total moles of ligand represented by the formula X-Sp-Z is in the range from about 50:1 to about 5:1.

In certain embodiments, the ligand represented by the formula X-Sp-Z comprises 3, 5-di-tert-butyl-4-hydroxybenzylphosphonic acid, a conjugate base of the acid, or a mixture including one or more of the foregoing.

In certain embodiments, the precursors are reacted in the presence of two or more chemically distinct ligands, at least two of said ligands being represented by the formula:

X-Sp-Z.

X, Sp, and Z are as described herein.

In certain embodiments, the precursors are reacted in the presence of two or more chemically distinct ligands, wherein
a first ligand is represented by the formula:

N-Sp-Z wherein N represents a primary amine group, a secondary amine group, an imidizole group, an amide group; and
a second ligand is represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group.

In such embodiments, Sp, and Z are as described herein, and wherein each of Sp and Z on the first ligand and on the second ligand can independently be the same or different.

In accordance with another aspect of the present invention, there is provided a composition including a nanoparticle taught herein and a host material.

In certain embodiments, the host material comprises a polymer. In certain embodiments, the host material comprises a resin. In certain embodiments, the host material is organic. In certain embodiments, the host material is inorganic.

Examples of host materials include, but are not limited to, acrylics, epoxies, silicones, polyurethanes, and materials useful in optical films and coatings.

In certain embodiments, a composition comprises light-emissive semiconductor nanocrystals dispersed in a host material, wherein at least a portion of the semiconductor nanocrystals include a ligand represented by the formula X-Sp-Z on an outer surface thereof, wherein Z includes at least three functional groups, at least one being selected to impart predetermined chemical miscibility properties to the nanocrystal in the host material. In such embodiments, use of mixing techniques such as sonicating/agitating, which can have a detrimental effect on an optical property (e.g., quantum efficiency) of the composition, can be reduced or avoided. (X, Sp and X are as described elsewhere herein.)

The inclusion of three or more functional groups of one or more predetermined character (e.g., including, but not limited to, polar, aliphatic, and/or aromatic groups) in one ligand can enhance the ability of the surface of the nanoparticle (e.g., a semiconductor nanocrystal) to interact favorably in a broad range of host materials. While not wishing to be bound by theory, it is believed that, in certain embodiments, such multifunctional ligand can reduce the enthalpy of interaction with the matrix material and allow nanoparticles including such ligand to be homogeneously incorporated into the host material.

A nanoparticle including a multifunctional ligand of the invention on at least a portion of an outer surface thereof can have a greater tendency to be readily dispersed in a desired host material.

In certain embodiments, by including a multifunctional ligand that is more compatible with a host material, the ligand can associate more favorably with the surface of the nanocrystal and not aggregate out of the host material. This can preserve the original emission efficiency of a light emissive nanoparticle (e.g., quantum dot or semiconductor nanocrystal). Furthermore, if ligands are compatible with the host material, additional ligands can be added to the host material to enhance and/or stabilize the emission efficiency of the nanocrystals in the matrix.

In certain embodiments, a composition of the invention can include a mixture of two or more nanoparticles taught herein, each of which is selected to emit at a predetermined wavelength or wavelength band which is distinct from that of the other(s) when excited (e.g., optically and/or electrically) to provide a desired light output. In certain embodiments, the nanoparticles comprise semiconductor nanocrystals.

In certain embodiments, a composition further includes one or more additives. In certain embodiments, the one or more additives can include a phosphor, a colorant, a scatterer, a binder, a surfactant, a UV absorber, and/or a mixture of one or more thereof.

In certain embodiments, a composition includes from about 0.001 to about 15 weight percent nanoparticles based on the weight of the host material.

In certain embodiments, the composition further comprises scatterers. In certain embodiments, the scatterers are included in the composition in an amount in the range from about 0.001 to about 15 weight percent of the weight of the host material. Preferably the host material comprises a solid (as opposed to a liquid) material.

In accordance with another aspect of the invention, there is provided a device including a nanoparticle in accordance with the invention. In certain embodiments, the device comprises a light-emitting device. In certain embodiments, the device comprises a photovoltaic device.

In accordance with another aspect of the invention, there is provided a device including a composition in accordance with the invention. In certain embodiments, the device comprises a light-emitting device. In certain embodiments, the device comprises a photovoltaic device.

As used herein, "native ligand" refers to a ligand that attaches or coordinates to a nanoparticle surface during the growth or overcoating thereof.

As used herein, functional groups are considered chemically distinct when they have different chemical compositions.

As used herein, ligands are considered chemically distinct when they have different chemical compositions.

The groups described herein as being represented by X also include substituted embodiments thereof that may include one or more aliphatic, aromatic, and/or other functional substituent groups, which may further be substituted with one or more additional functional groups.

In certain aspects and embodiments of the present invention, a nanoparticle can comprise a semiconductor material.

In certain aspects and embodiments of the present invention, a nanoparticle can comprise a core comprising a first material and a shell (or coating material) disposed over at least a portion of a surface of the core, the shell comprising a second material. In certain embodiments, the first material comprises a semiconductor material. In certain embodiments, the second material comprises a semiconductor material. In certain embodiments, one or more additional shells are disposed over at least a portion of a surface of the shell. A nanoparticle including a core and shell is also referred to as having a core/shell structure. In certain embodiments, a shell is disposed over all or substantially all of the outer surface. In certain embodiments, a nanoparticle can have a diameter of less than about 10 nanometers. In embodiments including a plurality of nanoparticles, the distribution of nanoparticles sizes is preferably monodisperse.

In certain preferred aspects and embodiments of the present invention, a nanoparticle comprises a semiconductor nanocrystal. (A semiconductor nanocrystal may also referred to herein as a quantum dot.) In certain embodiments, the semiconductor nanocrystal can comprise a core comprising a first material and a shell (or coating material) disposed over at least a portion of a surface of the core, the shell comprising a second material. Preferably, the second material comprises a nanocrystalline semiconductor material. In certain embodiments, one or more additional shells are disposed over at least a portion of a surface of the shell. Additional discussion of nanoparticles and semiconductor nanocrystals is provided elsewhere herein.

Preferred ligands comprise benzylphosphonic acid including at least two functional groups on the ring of the benzyl group (in addition to the Sp group), a conjugate base of such acid, and mixtures including one or more of the foregoing. In certain embodiments, a ligand comprises 4-hydroxybenzylphosphonic acid including at least one additional functional group on the ring of the benzyl group (in addition to the Sp group), a conjugate base of the acid, or a mixture of the foregoing. In certain embodiments, a ligand comprises 3,5-di-tent-butyl-4-hydroxybenzylphosphonic acid, a conjugate base of the acid, or a mixture of the foregoing.

Examples of ligands being represented by the formula X-Sp-Z can comprise an organic amine wherein Z comprises three chemically distinct functional groups. In certain embodiments, one of the functional groups comprises a terminal hydroxyl group. In certain embodiments, one of the functional groups comprises a halogen (e.g., F, Cl, Br, I).

In certain preferred embodiments, a nanoparticle comprises a semiconductor nanocrystal core comprising a first semiconductor material having an overcoating material comprising a second semiconductor material disposed on at least a portion of a surface of the core, wherein the overcoating material is grown thereon in the presence of one or more of the ligands represented by the formula X-Sp-Z described herein.

In certain embodiments of the methods described herein, the method is carried out in a liquid medium. Preferably, the liquid medium comprises a coordinating solvent or mixture of coordinating solvents. Examples of coordinating solvents including those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain aspects and embodiments of the inventions described or contemplated by this general description, the following detailed description, and claims, a nanoparticle is water insoluble or not dispersible in a liquid medium comprising water.

In certain aspects and embodiments of the inventions described or contemplated by this general description, the following detailed description, and claims, a nanoparticle comprising a semiconductor material (preferably, a semiconductor nanocrystal) is at least partially overcoated with a coating in the presence of one or more of the ligands taught herein. In certain embodiments, the coating comprises more than one material. In certain embodiments including a coating comprising more than one material, the materials are applied sequentially. In certain embodiments, a core can include multiple overcoats or shells disposed on a surface thereof. Each of the multiple overcoats or shells can comprise the same or different composition. In certain aspects and embodiments of the inventions described or contemplated by this general description, the following detailed description, and claims, a method is carried out in a non-aqueous medium. In certain preferred embodiments, the method is a colloidal synthesis method.

The foregoing, and other aspects and embodiments described herein all constitute embodiments of the present invention.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

The attached figures are simplified representations presented for purposes of illustration only; the actual structures may differ in numerous respects, including, e.g., relative scale, etc.

For a better understanding to the present invention, together with other advantages and capabilities thereof, reference is made to the following disclosure and appended claims in connection with the above-described drawings.

DETAILED DESCRIPTION OF THE INVENTION

In accordance with one aspect of the present invention, there is provided a nanoparticle including a ligand attached to a surface thereof, wherein the ligand is represented by the formula:

X-Sp-Z wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenate group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light (e.g., is not photo-curable).

Figure 1:
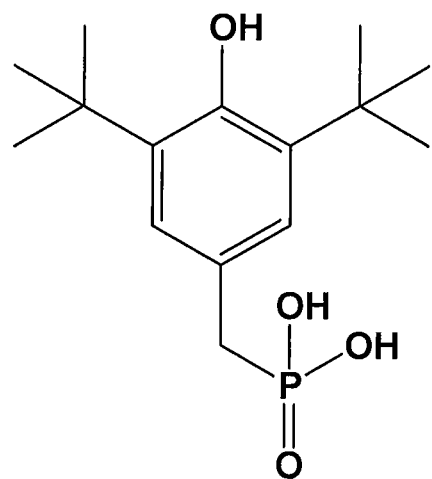
FIG. 1 represents the chemical structure of 3,5-di-tert-butyl-4-hydroxybenzylphosphonic acid, an example of a ligand included in certain embodiments of the invention.
Figure 2:
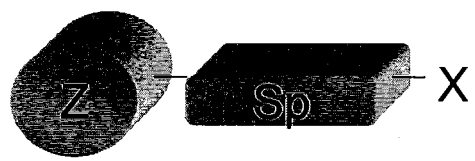
FIG. 2 schematically represents a ligand of the invention.
Figure 3:
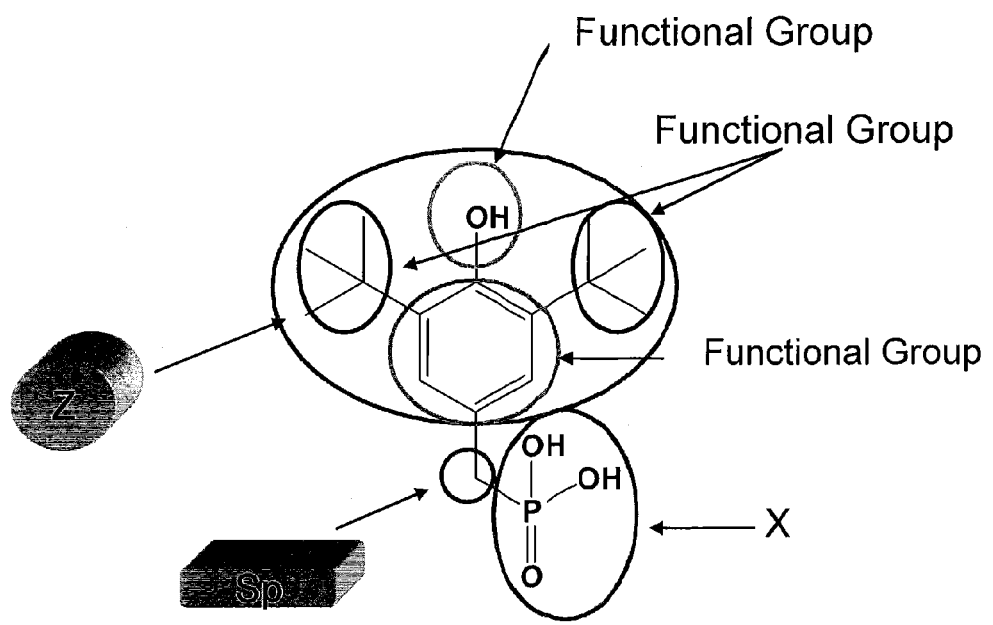
FIG. 3 provides an illustrative schematic of the ligand shown in FIG. 1.

FIG. 2 schematically represents a ligand of the invention. The X group has the ability to coordinate with the surface of the nanoparticle. In most embodiments, the ligand coordinates with the nanoparticle surface via the X group. In certain embodiments, the X group can further include an aliphatic or aromatic functional substituent group.

Sp represents a group capable of allowing a transfer of charge or an insulating group. (An Sp group may also be referred to herein as a spacer or as a spacer group.) Examples of Sp include, but are not limited to, a straight or branched $C_1$-$C_{20}$ hydrocarbon chains. In certain embodiments, the hydrocarbon chain includes at least one double bond, at least one triple bond, or at least one double bond and one triple bond. In certain embodiments, the hydrocarbon chain is interrupted by —O—, —S—, —N($R_a$)—, —N($R_a$)—C(O)—O—, —O—C(O)—N($R_a$)—, —N($R_a$)—C(O)—N($R_b$)—, —O—C(O)—O—, —P($R_a$)—, or —P(O)($R_a$)—, wherein each of $R_a$ and $R_b$, independently, is hydrogen, alkyl, alkenyl, alkynyl, alkoxy, hydroxylalkyl, hydroxyl, or haloalkyl. In certain embodiments, Sp can comprise an aromatic group. In certain embodiments, Sp can comprise an halogenated group. In certain embodiments, Sp can comprise a polar group. Other suitable spacer groups can be readily ascertained by one of ordinary skill in the relevant art.

In certain embodiments, Z includes one or more functional groups that exhibit dispersion bonding characteristics, polar bonding characteristics, and/or hydrogen bonding characteristics.

In certain embodiments, Z includes one or more functional groups that impart predetermined chemical miscibility properties to the nanoparticle to which it is attached.

In certain embodiments, Z includes one or more functional groups that exhibit polar, a halogen, aliphatic, and/or aromatic character.

Examples of functional groups that exhibit polar character include, but are not limited to, protic species such as hydroxyl, amino, carboxyl, etc. or polar a-protic species such as alkoxy, esters, amides, imides, nitriles, nitroso, etc. In certain embodiments, a halogenated functional group can be incorporated into a ligand by including a halogen substituent (e.g., F, Cl, Br, and I).

In certain embodiments, an aromatic functional group includes, but is not limited to phenyl, benzyl, naphthyl, biphenyl, fluorenyl, triarylamine, etc.

In certain embodiments, Z includes an heterocyclic ring, an aryl group, an aryl group condensed on one or several other aryl rings and/or alkyl and/or heterocyclic rings, a cycloalkyl group, a cycloalkyl alkyl group, an alkyl-cycloalkyl group, an arylalkyl group, an alkylaryl group, a heterocycloalkyl group or a alkyl-heterocycloalkyl group, wherein the group or ring includes one, two, or more functional groups attached thereto. In certain embodiments, a cycloalkyl group can be unsaturated and non-aromatic.

In certain embodiments, a functional group comprises an aliphatic functional group. Aliphatic groups generally include organic groups other than aromatic rings. Aliphatic groups can be cyclic (for example, but not limited to, cyclohexane, or acyclic (for example, but not limited to, hexane). Aliphatic groups can be saturated (including no double bonds between carbon atoms in the hydrocarbon chain.) Aliphatic groups can be unsaturated (e.g., including one or more double or triple bonds, but are not aromatic). In aliphatic groups, carbon atoms can be joined together in straight chains, branched chains, or non-aromatic rings (in which case they are called alicyclic). The carbon atoms can be joined by single bonds (alkanes), double bonds (alkenes), or triple bonds (alkynes). Besides hydrogen, other elements can be bound to the carbon chain, the most common being oxygen, nitrogen, sulfur, and chlorine.

In certain embodiments, an aliphatic group can further include one or more functional substituent groups, including, but not limited to, other functional groups described herein. Aliphatic groups include alkyl groups, alkenyl groups and alkynyl.

In certain embodiments, Z includes one or more aliphatic functional groups. An aliphatic group comprises a saturated hydrocarbon or unsaturated hydrocarbon group that can optionally be further substituted or functionalized. In certain embodiments, an aliphatic group includes, for example, but not limited to $C_{1-20}$ hydrocarbon. In certain embodiments, an aliphatic group comprises a $C_1$-$C_{20}$ hydrocarbon chain. In certain embodiments, an aliphatic group comprises a $C_2$-$C_{20}$ hydrocarbon. In certain embodiments, an aliphatic group is straight. In certain embodiments, an aliphatic group is branched, e.g., t-butyl, ethyl hexyl, etc. In certain embodiments, an aliphatic group can include at least one heteroatom. In certain embodiments, an aliphatic group comprises a $C_1$-$C_{20}$ alkyl hydrocarbon. In certain embodiments, the aliphatic group comprises a $C_2$-$C_{20}$ alkyl hydrocarbon. In certain embodiments, an alkyl group is branched. In certain embodiments, an alkyl group is straight. In certain embodiments, an alkyl group can include at least one hetero-atom.

In certain embodiments, a functional group can comprise an organic group (e.g., including, but not limited to, an aromatic or an aliphatic (a saturated or unsaturated non-aromatic, cyclic or non-cyclic) group that includes two or more functional substituent groups attached thereto.

In certain embodiments, Z includes an alkyl group including two or more functional substituent groups. In certain embodiments, the alkyl group is branched. In certain embodiments, the alkyl group is straight. In certain embodiments, the alkyl group comprises a $C_1$-$C_{20}$ hydrocarbon. In certain embodiments, the alkyl group comprises a $C_2$-$C_{20}$ hydrocarbon. In certain embodiments, an alkyl group can include at least one hetero-atom.

In certain embodiments, Z includes a cyclic group including two or more functional groups. In certain embodiments, a cyclic group can comprise a saturated or unsaturated cyclic (including, but not limited to, a single ring, a bicyclic structure, a multi-cyclic structure, etc.) compound or aromatic compound. In certain embodiments, a cyclic group can include at least one hetero-atom.

Examples of other functional groups for inclusion in Z also include, without limitation: bifunctional, and polyfunctional reagents (e.g., homobifunctional or heterobifunctional); reactive chemical groups (e.g., thiol, or carboxyl, hydroxyl, amino, amine, sulfo, and the like, carbodithioate, carbodithioic acid, thiourea, amide, phosphine oxide, phosphonic or phosphinic acid, thiophosphonic or thiophosphinic acid, which can be substituted with alkyl and/or aiyl units that are perhalogenated or partially halogenated; cyclic groups (including, but are not limited to, saturated or unsaturated cyclic or bicyclic compounds (e.g. cyclohexyl, isobornyl, etc.), or aromatic compounds (e.g. phenyl, benzyl, naphthyl, biphenyl, fluorenyl, triarylamine, etc.); a cyclic group including one or more substituent groups (including, for example, but not limited to, a reactive chemical group, an organic group (alky, aryl, etc.), etc.); halogenated groups (including, but not limited to, fluorinated groups, perfluorinated groups, (e.g. perfluoroalkyl, perfluorophenyl, perfluoroamines, etc.), chlorinated groups, perchlorinated groups; polar a-protic groups (including, but not limited to, alkoxy, ketones, esters, aldehydes, amides, ureas, urethanes, imines, etc.

In certain embodiments, at least one of the functional groups included in Z imparts predetermined chemical miscibility properties to the semiconductor nanocrystal to which it is attached.

In preferred certain embodiments, X, Sp, and Z are chemically distinct.

In certain embodiments, a nanoparticle comprises a semiconductor nanoparticle. In certain preferred embodiments, the nanoparticle comprises a semiconductor nanocrystal.

In certain embodiments, one or more additional chemically distinct ligands can be attached to a surface of the nanoparticle.

In certain embodiments, one or more of the additional chemically distinct ligands can be represented by the formula:

X-Sp-Z.

X, Sp, and Z are as described herein.

In certain embodiments in which two or more chemically distinct ligands represented by the formula X-Sp-Z are attached to the nanoparticle, a first ligand can be represented by the formula:

N-Sp-Z wherein N represents a primary amine group, a secondary amine group, an imidizole group, an amide group; and a second ligand can be represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group.

In such embodiments, Sp, and Z are as described herein. Each of Sp and Z on the first ligand and on the second ligand can independently be the same or different.

Examples of Sp and Z for inclusion in N-Sp-Z and Y-Sp-Z include, without limitation, those described herein. Sp and Z can be independently selected. Sp and Z included in each of the first and second ligands can independently be the same or different.

In certain embodiments, the nanoparticle comprises a semiconductor nanoparticle. In certain preferred embodiments, the nanoparticle comprises a semiconductor nanocrystal.

In accordance with another embodiment of the invention, there is provided a method for functionalizing a nanoparticle. The method comprises reacting precursors for forming a nanoparticle having a predetermined composition in the presence of a ligand represented by the formula:

X-Sp-Z, wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light.

In certain embodiments, Z represents a multifunctional group including a first functional group having at least two chemically distinct functional substituent groups attached thereto, the multifunctional group being capable of communicating a specific property or chemical reactivity to the nanoparticle.

Examples of X, Sp and Z include, without limitation, those described herein.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition.

In certain embodiments, the method is carried out in a liquid medium. Preferably, the liquid medium comprises a coordinating solvent or mixture of coordinating solvents. Examples of coordinating solvents include those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain embodiments, the mole ratio of total metal included in the one or more metal-containing precursors to total moles of ligand represented by the formula X-Sp-Z is in the range from about 1:0.1 to about 1:100. In certain embodiments, the mole ratio of total moles of metal included in the one or more metal-containing precursors to total moles of ligand represented by the formula X-Sp-Z is in the range from about 1:1 to about 1:50. In certain embodiments, the mole ratio of total moles of metal included in the one or more metal-containing precursors to total moles of ligand represented by the formula X-Sp-Z is in the range from about 1:1 to about 1:30.

In certain embodiments in which the method is carried out in a liquid medium, the mole ratio of total moles of the liquid medium to total moles of ligand represented by the formula X-Sp-Z is in the range from about 500:1 to about 2:1. In certain embodiments, the mole ratio of total moles of the liquid medium to total moles of ligand represented by the formula X-Sp-Z is in the range from about 100:1 to about 5:1. In certain embodiments, the mole ratio of total moles of the liquid medium to total moles of ligand represented by the formula X-Sp-Z is in the range from about 50:1 to about 5:1.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition.

In certain embodiments, the method comprises reacting precursors for forming a nanoparticle having a predetermined composition in the presence of two or more ligands represented by the formula:

X-Sp-Z.

X, Sp, and Z are as described herein.

In certain embodiments, the precursors are reacted in the presence of two or more chemically distinct ligands represented by the formula X-Sp-Z wherein a first ligand can be represented by the formula:

N-Sp-Z wherein N represents a primary amine group, a secondary amine group, an imidizole group, an amide group; and a second ligand can be represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group. Examples of Sp and Z include, without limitation, those described herein. Sp and Z can be independently selected. Sp and Z included in each of the first and second ligands can be the same or different.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition.

In accordance another embodiment of the invention, there is provided a method for overcoating at least a portion of a surface of a nanoparticle with a coating material having a predetermined composition, the method comprising reacting precursors for the predetermined composition in the presence of a ligand represented by the formula:

X-Sp-Z wherein:

X represents: a primary amine group, a secondary amine group, a urea, a thiourea, an imidizole group, an amide group, a carboxylic acid or carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein at least three of the functional groups are chemically distinct, and wherein Z is not reactive upon exposure to light.

In certain embodiments, Z represents a multifunctional group including a first functional group having at least two chemically distinct functional substituent groups attached thereto, the multifunctional group being capable of communicating a specific property or chemical reactivity to the nanoparticle.

In certain embodiments, the first functional group and at least two of the functional substituent groups are chemically distinct from each other.

In certain embodiments, the nanoparticle comprises a semiconductor nanoparticle. In certain preferred embodiments, the nanoparticle comprises a semiconductor nanocrystal. In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In certain embodiments, the method is carried out in a liquid medium. Preferably, the liquid medium comprises a coordinating solvent or mixture of coordinating solvents. Examples of coordinating solvents including those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain embodiments, the mole ratio of total metal included in the nanoparticles being overcoated to total moles of ligand represented by the formula X-Sp-Z is in the range from about 1:0.1 to about 1:100. In certain embodiments, the mole ratio of total moles of metal included in the nanoparticles being overcoated to total moles of ligand represented by the formula X-Sp-Z is in the range from about 1:1 to about 1:50. In certain embodiments, the mole ratio of total moles of metal included in the nanoparticles being overcoated to total moles of ligand represented by the formula X-Sp-Z is in the range from about 1:1 to about 1:30.

In certain embodiments of the method being carried out in a liquid medium, the mole ratio of total moles of the liquid medium to total moles of ligand represented by the formula X-Sp-Z is in the range from about 500:1 to about 2:1. In certain embodiments, the mole ratio of total moles of the liquid medium to total moles of ligand represented by the formula X-Sp-Z is in the range from about 100:1 to about 5:1. In certain embodiments, the mole ratio of total moles of the liquid medium to total moles of ligand represented by the formula X-Sp-Z is in the range from about 50:1 to about 5:1.

In certain embodiments, the nanoparticle comprises a semiconductor nanoparticle. In certain preferred embodiments, the nanoparticle comprises a semiconductor nanocrystal. In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In certain embodiments, the method comprising reacting precursors for the predetermined coating material in the presence of the nanoparticle to be coated and at least two chemically distinct ligands represented by the formula:

X-Sp-Z.

X, Sp, and Z are as described herein.

In certain embodiments, in which two or more chemically distinct ligands represented by the formula X-Sp-Z are included in the method, a first ligand can be represented by the formula:

N-Sp-Z wherein N represents a primary amine group, a secondary amine group, an imidizole group, an amide group; and a second ligand can be represented by the formula:

Y-Sp-Z wherein Y represents a carboxylic acid group, a carboxylate group, a phosphonic or arsonic acid group, a phosphoric acid group, a phosphate group, a phosphite group, a phosphinic acid group, a phosphinate group, a phosphine oxide group, a phosphinite group, a phosphine group, an arsenic acid group, an arsenate group, an arsenous acid group, an arsenite group, an arsinic acid group, an arsine oxide group, or an arsine group. Examples of Sp and Z include, without limitation, those described herein. Sp and Z can be independently selected. Sp and Z included in each of the first and second ligands can be the same or different.

Examples of Sp and Z include, without limitation, those described herein. Sp and Z can be independently selected. Sp and Z including in the two ligands can be the same or different.

In certain embodiments, the nanoparticle comprises a semiconductor nanoparticle. In certain preferred embodiments, the nanoparticle comprises a semiconductor nanocrystal.

In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In carrying out the methods described herein, the precursors are selected and reacted in amounts and under reaction conditions, and for a period of time, to produce a nanoparticle having the predetermined composition. Such variables can be routinely determined by a person of ordinary skill in the relevant art. In certain embodiments, the reaction is carried out in a controlled atmosphere (preferably in an atmosphere that is substantially free of water moisture and air). In certain preferred embodiments, the reaction is carried out in a water-free inert atmosphere.

To avoid the introduction of impurities which may have an unpredictable effect on the reaction, the ligands should preferably have a purity of at least 99 wt. %, and preferably greater than 99.5%.

In accordance with another aspect of the present invention, there is provided a composition including a nanoparticle taught herein and a host material.

In certain embodiments, the host material comprises a polymer. In certain embodiments, the host material comprises a resin. In certain embodiments, the host material is organic. In certain embodiments, the host material is inorganic.

Examples of host materials include, but are not limited to, acrylics, epoxies, silicones, polyurethanes, and materials useful in optical films and coatings.

Additional examples of a host material include monomers, binders, glasses, metal oxides, and other non-polymeric materials.

In certain embodiments, the host material is non-photoconductive.

In certain embodiments, an additive capable of dissipating charge is further included in the host material. In certain embodiments, the charge dissipating additive is included in an amount effective to dissipate any trapped charge. In certain embodiments, the host material is non-photoconductive and further includes an additive capable of dissipating charge, wherein the additive is included in an amount effective to dissipate any trapped charge.

Preferred host materials include polymeric and non-polymeric materials that are at least partially transparent, and preferably fully transparent, to pre-selected wavelengths of visible and non-visible light. In certain embodiments, the pre-selected wavelengths can include wavelengths of light in the visible (e.g., 400-700 nm), ultraviolet (e.g., 10-400 nm), and/or infrared (e.g., 700nm-12 µm) regions of the electromagnetic spectrum. Preferred host materials include cross-linked polymers and solvent-cast polymers.

Examples of preferred host materials include, but are not limited to, glass or a transparent resin. In particular, a resin such as a non-curable resin, heat-curable resin, or photocurable resin is suitably used from the viewpoint of processability. Specific examples of such a resin, in the form of either an oligomer or a polymer, include a melamine resin, a phenol resin, an alkyl resin, an epoxy resin, a polyurethane resin, a maleic resin, a polyamide resin, polymethyl methacrylate, polyacrylate, polycarbonate, polyvinyl alcohol, polyvinylpyrrolidone, hydroxyethylcellulose, carboxymethylcellulose, copolymers containing monomers forming these resins, and the like. Other suitable host materials can be identified by persons of ordinary skill in the relevant art.

In certain embodiments, a host material comprises a photocurable resin. A photocurable resin may be a preferred host material in certain embodiments in which the composition is to be patterned. As a photo-curable resin, a photo-polymerizable resin such as an acrylic acid or methacrylic acid based resin containing a reactive vinyl group, a photo-crosslinkable resin which generally contains a photo-sensitizer, such as polyvinyl cinnamate, benzophenone, or the like may be used.

A heat-curable resin may be used when the photo-sensitizer is not used. These resins may be used individually or in combination of two or more.

In certain embodiments a host material comprises a solvent-cast resin. A polymer such as a polyurethane resin, a maleic resin, a polyamide resin, polymethyl methacrylate, polyacrylate, polycarbonate, polyvinyl alcohol, polyvinylpyrrolidone, hydroxyethylcellulose, carboxymethylcellulose, copolymers containing monomers forming these resins, and the like can be dissolved in solvents known to those skilled in the art. Upon evaporation of the solvent, the resin forms a solid host material for the nanoparticles.

In certain embodiments, the composition including nanoparticles and a host material can be formed from an ink composition comprising nanoparticles and a liquid vehicle, wherein the liquid vehicle comprises a composition including one or more functional groups that are capable of being cross-linked. The functional units can be cross-linked, for example, by UV treatment, thermal treatment, or another cross-linking technique readily ascertainable by a person of ordinary skill in a relevant art. In certain embodiments, the composition including one or more functional groups that are capable of being cross-linked can be the liquid vehicle itself. In certain embodiments, it can be a co-solvent. In certain embodiments, it can be a component of a mixture with the liquid vehicle. In certain embodiments, the ink can further include scatterers.

In certain embodiments, nanoparticles (e.g., semiconductor nanocrystals) are distributed within the host material as individual particles.

In certain embodiments, nanoparticles are distributed within the host material may include flocculated (or aggregated) particles.

In certain embodiments, a composition comprises light-emissive semiconductor nanocrystals dispersed in a host material, wherein at least a portion of the semiconductor nanocrystals include a ligand represented by the formula X-Sp-Z on an outer surface thereof, wherein X, Sp, and Z are as described herein, and wherein at least one of the functional groups included in Z is selected to impart predetermined chemical miscibility properties to the nanocrystal in the host material. In such embodiments, use of mixing techniques such as sonicating/agitating, which can have a detrimental effect on an optical property (e.g., quantum efficiency) of the composition, can be reduced or avoided.

The inclusion of three or more functional groups of one or more predetermined character (e.g., polar, aliphatic, and/or aromatic groups) in one ligand can enhance the ability of the surface of the nanoparticle (e.g., a semiconductor nanocrystal) to interact favorably in a broad range of host materials. While not wishing to be bound by theory, it is believed that, in certain embodiments, such multifunctional ligand can reduce the enthalpy of interaction with the matrix material and allow nanoparticles including such ligand to be homogeneously incorporated into the host material.

A nanoparticle including one or more multifunctional ligands of the invention on at least a portion of an outer surface thereof can have a greater tendency to be readily dispersed in a desired host material.

In certain embodiments, by including a multifunctional ligand that is more compatible with a host material, the ligand can associate more favorably with the surface of the nanociystal and not aggregate out of the host material. This can preserve the original emission efficiency of a light emissive nanoparticle (e.g., quantum dot or semiconductor nanocrystal). Furthermore, if ligands are compatible with the host material, additional ligands can be added to the host material to enhance and/or stabilize the emission efficiency of the nanocrystals in the matrix.

In certain embodiments, a composition of the invention can include a mixture of two or more nanoparticles taught herein, each of which is selected to emit at a predetermined wavelength or wavelength band which is distinct from that of the other(s) when excited (e.g., optically and/or electrically) to provide a desired light output. In certain embodiments, the nanoparticles comprise semiconductor nanocrystals.

In certain embodiments, a composition further includes one or more additives. In certain embodiments, the one or more additives can include a phosphor, a colorant, a scatterer, a binder, a surfactant, a UV absorber, and/or a mixture of one or more thereof.

In certain embodiments, a composition includes from about 0.001 to about 15 weight percent nanoparticles based on the weight of the host material.

In certain embodiments, the composition further comprises scatterers. In certain embodiments, the scatterers are included in the composition in an amount in the range from about 0.001 to about 15 weight percent of the weight of the host material. Preferably the host material comprises a solid (as opposed to a liquid) material.

In accordance with another aspect of the invention, there is provided a device including a nanoparticle in accordance with the invention. In accordance with another aspect of the invention, there is provided a device including a composition in accordance with the invention.

The present invention will be further clarified by the following examples, which are intended to be exemplary of the present invention. In certain embodiments, a device comprises a display. In certain embodiments, a device comprises a solid state lighting device or other lighting unit. In certain embodiments, a device comprises a sign. In certain embodiments, a device comprises a photovoltaic device. In certain embodiments, a device comprises another electronic or optoelectronic device.

EXAMPLES

Example 1A

Preparation of Semiconductor Nanocrystals Capable of Emitting Red Light with
3,5-di-tert-butyl-4-hydroxybenzylphosphonic acid Synthesis of CdSe Cores:

1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Preparation of 3,5-Di-tert-butyl-4-hydroxybenzylphosphonic acid 3,5-Di-tert-butyl-4-hydroxybenzylphosphonic acid was obtained from PCI Synthesis, 9 Opportunity Way, Newbuiyport, Mass. 01950.

The preparation of 3,5-Di-tert-butyl-4-hydroxybenzylphosphonic acid utilized the following synthetic approach:

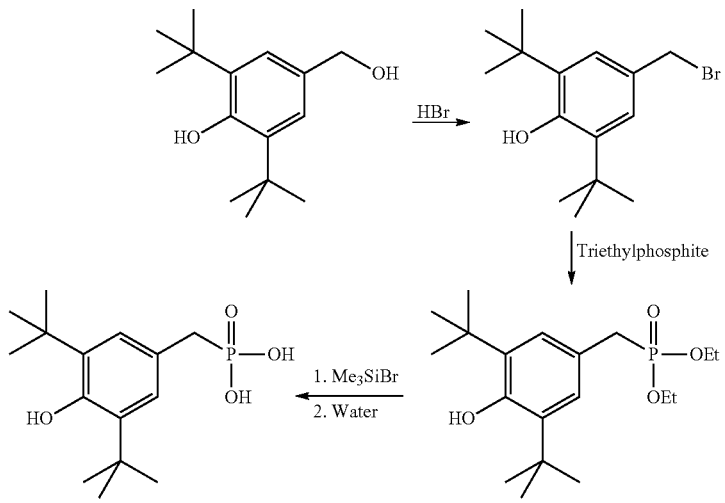

3,5-Di-tert-butyl-4-hydroxybenzylphosphonic acid can be characterized by the following:

Melting point: 199-200° C. [Lit: 200° C.; Literature ref: J. D. Spivack, FR1555941 (1969)] IR: 3614 cm$^{-1}$, 3593 cm$^{-1}$ (weak, O—H stretching).

$^1$H-NMR (CD$_3$OD): δ 7.10 (d, aromatic, 2H, $J_{P-H}$=2.6 Hz), 5.01 (s, exchanged HOD), 2.99 (d, —CH$_2$, 2H, $J_{P-H}$=21.2 Hz), 1.41 (s, —CH$_3$, 18H).

$^{13}$C-NMR (CD$_3$OD): δ 152.9 (aromatic), 137.9 (aromatic), 126.2 (aromatic), 123.5 (aromatic), 34.41 (d, —CH$_2$, 35.75, 33.07, $J_{P-C}$=537.2 Hz), 34.35 (—C(CH$_3$)$_3$), 29.7 (—C(CH$_3$)$_3$).

$^{31}$P-NMR (CD$_3$OD): δ 26.8

The above-identified synthetic precursors included in the preparation of 3,5-Di-tert-butyl-4-hydroxybenzylphosphonic acid can be characterized by the following:

Diethyl 3,5-di-tert-butyl-4-hydroxybenzylphosphonate

Melting point: 119-120° C. (Lit: 118-119° C.; Literature ref: R. K. Ismagilov, Zhur. Obshchei Khimii, 1991, 61, 387).

IR: 3451 cm$^{-1}$ (weak, —OH, stretching), 2953 (weak, —CH$_3$, C—H stretching).

$^1$H-NMR (CDCl$_3$): δ 6 7.066 (d, Ar—H, 2H, $J_{P-H}$=2.8 Hz), 5.145 (s, 1H, —OH), 4.06-3.92 (m, —CH$_2$CH$_3$, 4H, H—H and long-range P—H couplings), 3.057 (d, Ar—CH$_2$, 2H, $J_{P-H}$=21.0Hz), 1.412 (s, —C(CH$_3$)$_3$, 18H), 1.222 (t, —CH$_2$CH$_3$, 6H).

$^{13}$C-NMR (CDCl$_3$): δ 153.98 (aromatic), 136.22 (aromatic), 126.61 (aromatic), 122.07 (aromatic), 62.14 (—OCH$_2$CH$_3$, $J_{P-C}$=24.4 Hz), 33.63 (Ar—CH$_2$, $J_{P-C}$=552.4 Hz), 34.53 [—C(CH$_3$)$_3$], 30.54 [—C(CH$_3$)$_3$], 16.66 (—CH$_2$CH$_3$, $J_{P-C}$=24.4 Hz).

$^{31}$P-NMR (CDCl$_3$): δ 28.43.

3,5-di-tert-butyl-4-hydroxybenzyl bromide

Melting point: 51-54° C. (Lit: 52-54° C.; Literature ref: J. D. McClure, J. Org. Chem., 1962, 27, 2365)

IR: 3616 cm$^{-1}$ (medium, O—H stretching), 2954 cm$^{-1}$ (weak, alkyl C—H stretching).

$^1$H-NMR (CDCl$_3$): δ 7.20 (s, Ar—H, 2H), 5.31 (s, —OH), 4.51 (s, —CH$_2$, 2H), 1.44 {s, [—C(CH$_3$)$_3$], 18H}.

$^{13}$C-NMR (CDCl$_3$): δ 154.3 (aromatic), 136.5 (aromatic), 128.7 (aromatic), 126.3 (aromatic), 35.8 [(—C(CH$_3$)$_3$], 34.6 (—CH$_2$), 30.5 [—C(CH$_3$)$_3$].

Other synthetic approaches that are known or readily ascertainable by one of ordinary skill in the relevant art can be used to prepare 3,5-Di-tert-butyl-4-hydroxybenzylphosphonic acid.

Synthesis of CdSe/CdZnS Core-Shell Nanocrystals:

25.86 mmol of trioctylphosphine oxide and 2.4 mmol of 3,5-di-tert-butyl-4-hydroxybenzylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in chloroform and used to make semiconductor nanocrystal composite materials.

In Table 1 (below), the 3,5-di-tert-butyl-4-hydroxybenzylphosphonic acid ligand group is referred to as BHT.

Example 1B

Preparation of Layer including Semiconductor Nanocrystals

Films listed in Table 1 (below) are prepared using samples including semiconductor nanocrystals prepared substantially in accordance with the synthesis described in Example 1A. Bulk chloroform is removed from the nanocrystal samples with nitrogen purging. Residual chloroform is removed from the semiconductor nanocrystals under vacuum at room temperature. Care is taken not to over dry or completely remove all solvent.

37 ml of RD-12, a low viscosity reactive diluent commercially available from Radcure Corp, 9 Audrey Pl, Fairfield, N.J. 07004-3401, United States, is added to 4.68 gram of semiconductor nanocrystals under vacuum. The vessel is then backfilled with nitrogen and the mixture is mixed using a vortex mixer. After the semiconductor nanocrystals are pre-solubilized in the reactive diluent, 156 ml of DR-150, an UV-curable acrylic formulation commercially available Radcure, is added slowly under vacuum. The vessel is then backfilled with nitrogen and the mixture is mixed using a vortex mixer.

2.00 gram $TiO_2$ (if indicated in Table 1 as being included) is next added and the mixture is mixed with an homogenizer.

12.00 gram curing agent Escacure TPO is added, following which the mixture is mixed with an homogenizer. The vessel including the mixture is then wrapped with black tape to shield the fluid from light.

The vessel in then backfilled with nitrogen and sonified for at least about 3 hours. Care is taken to avoid temperatures over 40° C. while the sample is in the ultrasonic bath.

Samples are coated by Mayer rod on precleaned glass slides and cured in a 5000-EC UV Light Curing Flood Lamp from DYMAX Corporation system with an H-bulb (225 mW/cm$^2$) for 10 seconds.

A sample is removed for evaluation and coated on a glass slide with a 52 rod and cured for 10 sec:

Thickness=72 μm

Lambda em=633.1 nm FWHM=36 nm

% EQE=50.0% % $A_{450\,nm}$=82.6%

Occasionally, the mixing vial is heated to lower viscosity and aid stirring. After the addition is competed, vacuum is pulled to remove entrained air. The vial is then placed in an ultrasonic bath (VWR) from 1 hour to overnight, resulting in a clear, colored solution. Care is taken to avoid temperatures over 40° C. while the sample is in the ultrasonic bath.

Multiple batches of the semiconductor nanocrystals of the same color are mixed together prior to making the acrylic preparation.

Samples that include multiple layers in order to achieve the desired thickness undergo a cure step between the formation of the separate layers. Samples including one or more filters on top of (or below) the layers including host material and nanoparticles have the filters coated by Mayer rod in one or more separate step.

Filters are made by blending UV-curable pigment ink formulations from Coates/Sun Chemical. (Examples include, but are not limited to, DXT-1935 and WIN99.) A filter composition is formulated by adding the weighted absorbances of the individual colors together to achieve the desired transmission characteristics.

TABLE 1

| Film Color/Sample # (Nanocrystal Prep. Example #) | Solvent | Ligand(s) | Emission (nm) | FWHM | Film EQE (%) |
|---|---|---|---|---|---|
| Red/Sample #1 (without TiO2) (Ex. 1) | Chloroform | BHT | 631 | 36 | 29.0 |
| Red/Sample #2 (with TiO2) (Ex. 1) | Chloroform | BHT | 633 | 36 | 50.0 |

Film Characterization:

The films are characterized in the following ways:

Thickness: measured by a micrometer

Emission measurement measured on sample 1 of each type, on Cary Eclipse. Excitation at 450 nm, 2.5 nm excitation slit, 5 nm emission slit.

Absorption measured at 450 nm on sample 1 of each type, on Cary 5000. Baseline corrected to blank glass slide.

CIE coordinates measured on sample 1 of each type using CS-200 Chroma Meter. Sample excited with 450 nm LED, and camera collected color data off axis.

Figure 4:
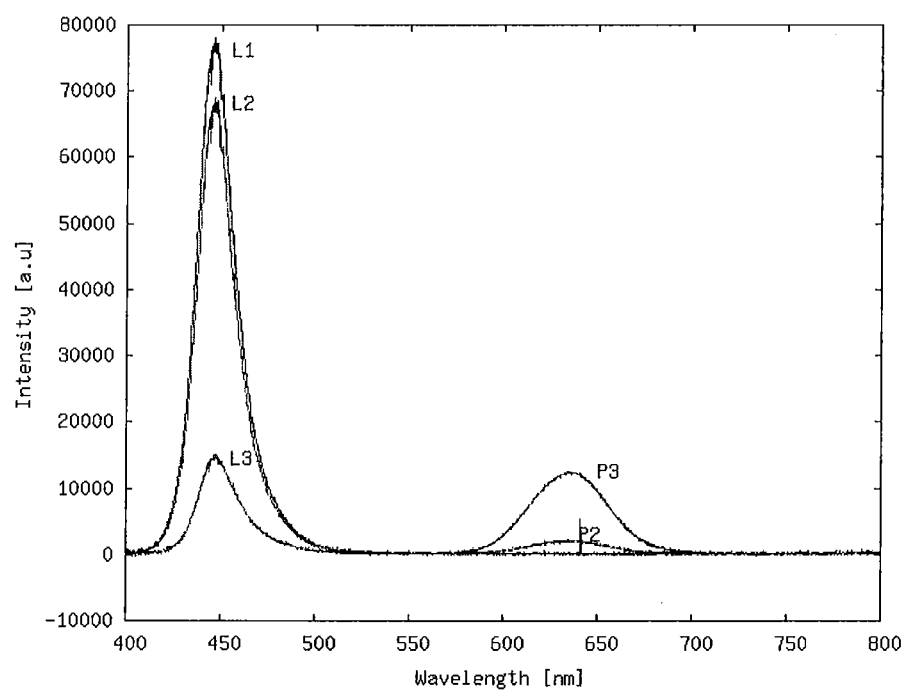
FIG. 4 depicts spectra to illustrate a method for measuring quantum efficiency.

The external photoluminescent (PL) quantum efficiency is measured using the method developed by Mello et al. (cited below). The method uses a collimated 450 nm LED source, an integrating sphere and a spectrometer. Three measurements are taken. First, the LED directly illuminates the integrating sphere giving the spectrum labeled L1 in FIG. 4. Next, the PL sample is placed into the integrating sphere so that only diffuse LED light illuminates the sample giving the (L2+P2) spectrum depicted in FIG. 4. Finally, the PL sample is placed into the integrating sphere so that the LED directly illuminates the sample (just off normal incidence) giving the (L3+P3) spectrum depicted in FIG. 4. After collecting the data, each spectral contribution (L's and P's) is computed. L1, L2 and L3 correspond to the sums of the LED spectra for each measurement and P2 and P3 are the sums associated with the PL spectra for 2nd and 3rd measurements. The following equation then gives the external PL quantum efficiency:

$$EQE=[(P3 \cdot L2)\mathrm{minus}(P2 \cdot L3)]/(L1 \cdot (L2\ \mathrm{minus}\ L3))$$

For additional information concerning EQE measurements, see Mello et al., Advanced Materials 9(3):230 (1997), which is hereby incorporated by reference.

Example 2A

Preparation of Semiconductor Nanocrystals Capable of Emitting Red Light with 3,5-di-tert-butyl-4-hydroxybenzylphosphonic acid Synthesis of CdSe Cores:

1 mmol cadmium acetate is dissolved in 8.96 mmol of tri-n-octylphosphine at 100° C. in a 20 mL vial and is then dried and degassed for one hour. 15.5 mmol of trioctylphosphine oxide and 2 mmol of octadecylphosphonic acid are added to a 3-neck flask and dried and degassed at 140° C. for one hour. After degassing, the Cd solution is added to the oxide/acid flask and the mixture is heated to 270° C. under nitrogen. Once the temperature reaches 270° C., 8 mmol of tri-n-butylphosphine is injected into the flask. The temperature is brought back to 270° C. where 1.1 mL of 1.5 M TBP-Se is then rapidly injected. The reaction mixture is heated at 270° C. for 15-30 minutes while aliquots of the solution are removed periodically in order to monitor the growth of the nanocrystals. Once the first absorption peak of the nanocrystals reaches 565-575 nm, the reaction is stopped by cooling the mixture to room temperature. The CdSe cores are precipitated out of the growth solution inside a nitrogen atmosphere glovebox by adding a 3:1 mixture of methanol and isopropanol. The cores are isolated and then dissolved in hexane for use in making core-shell materials.

Preparation of
3,5-Di-tert-butyl-4-hydroxybenzylphosphonic acid 3,5-Di-tert-butyl-4-hydroxybenzylphosphonic acid is obtained from PCI Synthesis, 9 Opportunity Way, Newburyport, Mass. 01950 and is prepared generally as described in Example 1A above.

Synthesis of CdSe/CdZnS Core-Shell Nanocrystals:

25.86 mmol of trioctylphosphine oxide and 2.4 mmol of 3,5-di-tert-butyl-4-hydroxybenzylphosphonic acid are loaded into a four-neck flask. The mixture is then dried and degassed in the reaction vessel by heating to 120° C. for about an hour. The flask is then cooled to 75° C. and the hexane solution containing isolated CdSe cores (0.1 mmol Cd content) is added to the reaction mixture. The hexane is removed under reduced pressure. Dimethyl cadmium, diethyl zinc, and hexamethyldisilathiane are used as the Cd, Zn, and S precursors, respectively. The Cd and Zn are mixed in equimolar ratios while the S is in two-fold excess relative to the Cd and Zn. The Cd/Zn and S samples are each dissolved in 4 mL of trioctylphosphine inside a nitrogen atmosphere glove box. Once the precursor solutions are prepared, the reaction flask is heated to 155° C. under nitrogen. The precursor solutions are added dropwise over the course of 2 hours at 155° C. using a syringe pump. After the shell growth, the nanocrystals are transferred to a nitrogen atmosphere glovebox to be precipitated out of the growth solution by adding a 3:1 mixture of methanol and isopropanol. The core-shell nanocrystals are then isolated and dispersed in fluorobenzene and used to make an optical material.

(3,5-di-tert-butyl-4-hydroxybenzylphosphonic acid ligand group may also be referred to herein as BHT.)

Example 2B

Preparation of Optical Component Including Semiconductor Nanocrystals

The film listed in the Table 2 below is prepared using optical material including semiconductor nanocrystals (prepared substantially in accordance with the synthesis described in Example 2A).

The red-emitting semiconductor nanocrystals dispersed in solvent have a peak emission at 609 nm, a FWHM of 31, a solution quantum yield of 77% and a concentration of 21 mg/ml.

0.5 ml of RD-12, a low viscosity reactive diluent commercially available from Radcure Corp, 9 Audrey Pl, Fairfield, N.J. 07004-3401, United States, is added to a 20 ml septum capped vial including a magnetic stirrer bar, the system is closed and purged through a syringe needle under vacuum then backfilled with nitrogen. 2.6 ml of the 21 mg/ml suspension of the red-emitting nanocrystals is added to the vial by a 3 ml syringe. Solvent is removed from the vial by vacuum stripping. 2 ml of DR-150 is then added to the vial through a syringe and the mixture is mixed using a Vortex mixer. (DR-150 is a UV-curable acrylic formulation commercially available from Radcure.). The vessel is then backfilled with nitrogen and the mixture is mixed using a Vortex mixer.

0.028 gram $TiO_2$ is next added to the open vial and the mixture is mixed with a Vortex mixer followed by mixing with an homogenizer.

The vial is then capped and deaerated under vacuum and backfilled with nitrogen.

After mixing, the closed vial is put in an ultrasonic bath for 50 minutes. Care is taken to avoid temperatures over 40° C. while the sample is in the ultrasonic bath.

The sample is stored in the dark until used to make a coating.

Tego 2500 is added before forming films on polycarbonate.

Sample material from the vial is Mayer rod coated onto a corona treated precleaned 1 mm thick sheet of transparent polycarbonate and cured in a 5000-EC UV Light Curing Flood Lamp from DYMAX Corporation system with an H-bulb (225 mW/cm$^2$) for 20 seconds. The thickness of the nanocrystal containing layer on the polycarbonate is approximately 30 microns.

The resulting film is cut to size to serve as cover plates on white light emitting Array PAR 30 LED lamps available from NEXXUS Lighting.

Data for Array PAR 30 LED lamps (available from NEXXUS Lighting) with and without an optical component comprising the above-prepared cover plates is provided in the following Table 2:

TABLE 2

| | LUMENS | CORRELATED COLOR TEMPERATURE | GENERAL CRI ($R_a$) |
|---|---|---|---|
| Array PAR 30 LED Lamp (5000K) without nanocrystal containing cover plate | 342 | 5079 | 76.4 |
| Array PAR 30 LED Lamp (5000K) with nanocrystal containing cover plate (as described in above example 2B) | 220 | 2712 | 89.6 |
| Array PAR 30 LED Lamp (6500K) without nanocrystal containing cover plate | 366 | 6412 | 75.7 |
| Array PAR 30 LED Lamp (6500K) with nanocrystal containing cover plate (as described in above example 2B) | 224 | 3031 | 91.3 |

Example 3A

Preparation of Semiconductor Nanocrystals Capable of Emitting 611 nm Light with 3,5-di-tert-butyl-4-hydroxybenzylphosphonic acid Synthesis of CdSe Cores:

29.9 mmol cadmium acetate is dissolved in 436.7 mmol of tri-n-octylphosphine at 100° C. in a 250 mL 3-neck round-bottom flask and then dried and degassed for one hour. 465.5 mmol of trioctylphosphine oxide and 61.0 mmol of octadecylphosphonic acid are added to a 0.5 L glass reactor and dried and degassed at 140° C. for one hour. After degassing, the Cd solution is added to the reactor containing the oxide/acid and the mixture is heated to 270° C. under nitrogen. Once the temperature reaches 270° C., 243.2 mmol of tri-n-butylphosphine is injected into the flask. The temperature is brought back to 270° C. where 34 mL of 1.5 M TBP-Se is then rapidly injected. The reaction mixture is heated at 250° C. for 9 minutes at which point the heating mantle is removed from the reaction flask and the solution is allowed to cool to ambient temperature. Once the first absorption peak of the nanocrystals reaches about 558 nm, the reaction is stopped by cooling the mixture to room temperature. The CdSe cores are precipitated out of the growth solution inside a nitrogen atmosphere glovebox by adding a 3:1 mixture of methanol and isopropanol. The isolated cores are then dissolved in hexane and used to make core-shell materials.

Synthesis of CdSe/CdZnS Core-Shell Nanocrystals:

Two identical reactions are set up whereby 25.86 mmol of trioctylphosphine oxide and 2.4 mmol of 3,5-di-tert-butyl-4-hydroxybenzylphosphonic acid are loaded into 50 mL four-neck round bottom flasks. The mixtures are then dried and degassed in the reaction vessels by heating to 120° C. for about an hour. The flasks are then cooled to 70° C. and the hexane solution containing isolated CdSe cores (0.096 mmol Cd content) are added to each reaction mixture. The hexane is removed under reduced pressure. Dimethyl cadmium, diethyl zinc, and hexamethyldisilathiane are used as the Cd, Zn, and S precursors, respectively. The Cd and Zn are mixed in equimolar ratios while the S is in two-fold excess relative to the Cd and Zn. Two sets of Cd/Zn (0.29 mmol of dimethylcadmium and diethylzinc) and S (1.15 mmol of hexamethyldisilathiane) samples are each dissolved in 4 mL of trioctylphosphine inside a nitrogen atmosphere glove box. Once the precursor solutions are prepared, the reaction flasks are heated to 155° C. under nitrogen. The Cd/Zn and S precursor solutions are added dropwise to the respective reaction flasks over the course of 2 hours at 155° C. using a syringe pump. After the shell growth, the nanocrystals are transferred to a nitrogen atmosphere glovebox and precipitated out of the growth solution by adding a 3:1 mixture of methanol and isopropanol. The isolated core-shell nanocrystals are then dispersed in toluene.

Example 3B

Preparation of Optical Component including Semiconductor Nanocrystals

The following film is prepared using optical material including semiconductor nanocrystals (prepared substantially in accordance with the synthesis described in Example 3A).

The semiconductor nanocrystals comprise red-emitting semiconductor nanocrystals dispersed in toluene and have a peak emission at 611 nm, a FWHM of about 32 nm, a solution quantum yield of 70% and a concentration of 20.4 mg/ml.

5.5 ml of the 20.4 mg/ml suspension of the red-emitting nanocrystals is added from a 6 mL syringe to a 20 ml septum capped vial including a magnetic stirrer bar, the system is closed and purged through a syringe needle under vacuum then backfilled with nitrogen. Approximately half of the solvent is removed from the vial by vacuum stripping. 1.0 ml of RD-12, a low viscosity reactive diluent commercially available from Radcure Corp, 9 Audrey Pl, Fairfield, N.J. 07004-3401 is added. 4.0 ml of DR-150 is then added to the vial through a syringe and the mixture is mixed using a Vortex mixer. (DR-150 is a UV-curable acrylic formulation commercially available from Radcure.)

0.3 ml of a 10% solution of Tego 2500 in toluene is added to the mixture by syringe while mixing. Remaining solvent is removed from the vial by vacuum stripping.

The vessel is then backfilled with nitrogen and the mixture is mixed using a Vortex mixer.

0.056 gram $TiO_2$ (Ti-Pure 902+ available from DuPont) is next added to the open vial and the mixture is mixed with a Vortex mixer followed by mixing with an homogenizer.

The vial is then capped and deaerated under vacuum and backfilled with nitrogen.

After mixing, the closed vial is put in an ultrasonic bath for 50 minutes. Care is taken to avoid temperatures over 40° C. while the sample is in the ultrasonic bath.

The sample is stored in the dark until used to make a coating.

Sample material from the vial is screen-printed onto a corona treated pre-cleaned (using an isopropanol wipe) 1.4 mm thick polycarbonate (1% transmission haze) hexagonal cover plate and cured in a 5000-EC UV Light Curing Flood Lamp from DYMAX Corporation system with an H-bulb (225 mW/cm$^2$) for 20 seconds. The thickness of the nanocrystal containing layer on the polycarbonate is approximately 32 microns.

The resulting cover plate is included as the face plate of a white light emitting Array PAR 30 LED lamp available from NEXXUS Lighting.

Example 4

Preparation of Semiconductor Nanocrystals

Example 4A

Preparation of Semiconductor Nanocrystals Capable of Emitting 588 nm Light with 3,5-di-tert-butyl-4-hydroxybenzylphosphonic acid Synthesis of CdSe Cores: 1.75 mmol cadmium acetate is dissolved in 15.7 mmol of tri-n-octylphosphine at 140° C. in a 20 mL vial and then dried and degassed for one hour. 31.0 mmol of trioctylphosphine oxide and 4 mmol of octadecylphosphonic acid are added to a 3-neck flask and dried and degassed at 110° C. for one hour. After degassing, the Cd solution is added to the oxide/acid flask and the mixture is heated to 270° C. under nitrogen. Once the temperature reaches 270° C., 16 mmol of tri-n-butylphosphine is injected into the flask. The temperature is brought back to 270° C. where 2.3 mL of 1.5 M TBP-Se is then rapidly injected. The reaction mixture is heated at 270° C. for 30 seconds and then the heating mantle is removed from the reaction flask allowing the solution to cool to room temperature. The CdSe cores are precipitated out of the growth solution inside a nitrogen atmosphere glovebox by adding a 3:1 mixture of methanol and isopropanol. The isolated cores are then dissolved in hexane and used to make core-shell materials. (Abs/Emission/FWHM (nm)=518/529/26.5).

Synthesis of CdSe/CdZnS Core-Shell Nanocrystals: Two identical reactions are set up whereby 25.86 mmol of trioctylphosphine oxide and 2.4 mmol of 3,5-di-tert-butyl-4-hydroxybenzylphosphonic acid are loaded into 50 mL four-neck round bottom flasks. The mixtures are then dried and degassed in the reaction vessels by heating to 120° C. for about an hour. The flasks are then cooled to 70° C. and the hexane solution containing isolated CdSe cores from above (0.062 mmol Cd content) are added to the respective reaction mixture. The hexane is removed under reduced pressure. Dimethyl cadmium, diethyl zinc, and hexamethyldisilathiane are used as the Cd, Zn, and S precursors, respectively. The Cd and Zn are mixed in equimolar ratios while the S was in two-fold excess relative to the Cd and Zn. Two sets of Cd/Zn (0.31 mmol of dimethylcadmium and diethylzinc) and S (1.24 mmol of hexamethyldisilathiane) samples are each dissolved in 4 mL of trioctylphosphine inside a nitrogen atmosphere glove box. Once the precursor solutions are prepared, the reaction flasks are heated to 155° C. under nitrogen. The Cd/Zn and S precursor solutions are added dropwise to the respective reaction flasks over the course of 2 hours at 155° C. using a syringe pump. After the shell growth, the nanocrystals are transferred to a nitrogen atmosphere glovebox and precipitated out of the growth solution by adding a 3:1 mixture of methanol and isopropanol. The isolated core-shell nanocrystals are then dispersed in toluene and the solutions from the two batches are combined Example 4B Preparation of Semiconductor Nanocrystals Capable of Emitting 632 nm Light with 3,5-di-tert-butyl-4-hydroxybenzylphosphonic acid Synthesis of CdSe Cores: 29.9 mmol cadmium acetate is dissolved in 436.7 mmol of tri-n-octylphosphine at 140° C. in a 250 mL 3-neck round-bottom schlenk flask and then dried and degassed for one hour. 465.5 mmol of trioctylphosphine oxide and 61.0 mmol of octadecylphosphonic acid are added to a 0.5 L glass reactor and dried and degassed at 120° C. for one hour. After degassing, the Cd solution is added to the reactor containing the oxide/acid and the mixture is heated to 270° C. under nitrogen. Once the temperature reaches 270° C., 243.2 mmol of tri-n-butylphosphine is injected into the flask. The temperature is brought back to 270° C. where 33.3 mL of 1.5 M TBP-Se is then rapidly injected. The reaction mixture is heated at 270° C. for ~9 minutes at which point the heating mantle is removed from the reaction flask and the mixture is allowed to cool to room temperature. The CdSe cores are precipitated out of the growth solution inside a nitrogen atmosphere glovebox by adding a 3:1 mixture of methanol and isopropanol. The isolated cores are then dissolved in hexane and used to make core-shell materials. (Abs/Emission/FWHM (nm)=571/592/45)

Synthesis of CdSe/CdZnS Core-Shell Nanocrystals: Three identical reactions are conducted whereby 517.3 mmol of trioctylphosphine oxide and 48.3 mmol of 3,5-di-tert-butyl-4-hydroxybenzylphosphonic acid are loaded into a 0.5 L glass reactor. The mixtures are then dried and degassed in the reactor by heating to 120° C. for about an hour. The reactors are then cooled to 70° C. and hexane solutions containing the isolated CdSe cores from above (1.95 mmol Cd content) are added to the respective reaction mixtures. The hexane is removed under reduced pressure. Dimethyl cadmium, diethyl zinc, and hexamethyldisilathiane are used as the Cd, Zn, and S precursors, respectively. The Cd and Zn are mixed in equimolar ratios while the S was in two-fold excess relative to the Cd and Zn. Two sets of Cd/Zn (5.5 mmol of dimethylcadmium and diethylzinc) and S (22 mmol of hexamethyldisilathiane) samples are each dissolved in 80 mL of trioctylphosphine inside a nitrogen atmosphere glove box. Once the precursor solutions are prepared, the reaction flasks are heated to 155° C. under nitrogen. The precursor solutions are added dropwise the respective reactor solutions over the course of 2 hours at 155° C. using a syringe pump. After the shell growth, the nanocrystals are transferred to a nitrogen atmosphere glovebox and precipitated out of the growth solution by adding a 3:1 mixture of methanol and isopropanol. The resulting precipitates are then dispersed in hexane and precipitated out of solution for a second time by adding a 3:1 mixture of methanol and isopropanol. The isolated core-shell nanocrystals are then dissolved in chloroform and the solutions from the three batches are mixed. (Abs/Emission/FWHM (nm)=610/632/40)

Example 5

Preparation of Optical Component including Two Different Types of Semiconductor Nanocrystals The following film is prepared using optical material including semiconductor nanocrystals (prepared substantially in accordance with the synthesis described in Example 4A).

A. Optical Material including Semiconductor Nanocrystals with a Peak Emission in the Orange Spectral Region:

The semiconductor nanocrystals prepared substantially in accordance with the synthesis described in Example 4A comprise orange-emitting semiconductor nanocrystals dispersed in Fluorobenzene have a peak emission at 588 nm, a FWHM of about 28 nm, a solution quantum yield of 83% and a concentration of 20 mg/ml.

2.7 ml of the 20 mg/ml suspension of the orange-emitting nanocrystals is added from a 3 mL syringe to a 20 ml septum capped vial including a magnetic stirrer bar, the system is closed and purged through a syringe needle under vacuum then backfilled with nitrogen. Approximately 90 percent of the solvent is removed from the vial by vacuum stripping. 0.5 ml of RD-12, a low viscosity reactive diluent commercially available from Radcure Corp, 9 Audrey Pl, Fairfield, N.J. 07004-3401 is added. Remaining solvent is removed from the vial by vacuum stripping. 2.0 ml of DR-150 is then added to the vial through a syringe and the mixture is mixed using a Vortex mixer. (DR-150 is a UV-curable acrylic formulation commercially available from Radcure.). The mixture is then placed in an ultrasonic bath for approximately 15 minutes.

0.028 gram $TiO_2$ (Ti-Pure 902+ available from DuPont) is next added to the open vial and the mixture is mixed with a Vortex mixer followed by mixing with an homogenizer.

The vial is then capped and deaerated under vacuum and backfilled with nitrogen.

After mixing, the closed vial is put in an ultrasonic bath for 50 minutes. Care is taken to avoid temperatures over 40° C. while the sample is in the ultrasonic bath.

The sample is stored in the dark until used to make a combined formulation with long wavelength semiconductor and additional matrix material.

B. Optical Material Including Semiconductor Nanocrystals with a Peak Emission in the Red Spectral Region:

The semiconductor nanocrystals prepared substantially in accordance with the synthesis described in Example 4B comprise red-emitting semiconductor nanocrystals dispersed in Chloroform and have a peak emission at 632 nm, a FWHM of about 40 nm, a solution quantum yield of 70% and a concentration of 56.7 mg/ml.

99 ml of the 56.7 mg/ml suspension of the red-emitting nanocrystals is added to a septum capped Erlenmeyer flask including a magnetic stirrer bar, the system is closed and purged through a syringe needle under vacuum then backfilled with nitrogen. Approximately 95 percent of the solvent is removed from the vial by vacuum stripping. 46.6 ml of RD-12, a low viscosity reactive diluent commercially available from Radcure Corp, 9 Audrey Pl, Fairfield, N.J. 07004-3401 is added. Remaining solvent is removed from the vial by vacuum stripping. 187 ml of DR-150 is then added to the vial through a syringe and the mixture is mixed using a Vortex mixer. (DR-150 is a UV-curable acrylic formulation commercially available from Radcure.). The mixture is then placed in an ultrasonic bath for approximately 50 minutes.

Approximately 2.6 gram $TiO_2$ (Ti-Pure 902+ available from DuPont) is next added to the open vial as well as 12.9 grams of Esacure TPO previously ground to reduce particle size in a ball mill machine and the mixture is mixed with a Vortex mixer followed by mixing with an homogenizer.

The vial is then capped and deaerated under vacuum and backfilled with nitrogen.

After mixing, the closed vial is put in an ultrasonic bath for 60 minutes. Care is taken to avoid temperatures over 40° C. while the sample is in the ultrasonic bath. The sample is stored in the dark until used to make a combined formulation with long wavelength semiconductor and additional matrix material.

C. Preparation of Host Material Including Spacer beads:

0.9 ml of RD-12, a low viscosity reactive diluent commercially available from Radcure Corp, 9 Audrey Pl, Fairfield, N.J. 07004-3401 and 3.8 ml of DR-150, also available from Radcure Corp, is added to a 20 ml vial and the mixture is mixed using a Vortex mixer. The mixture is then placed in an ultrasonic bath for approximately 30 minutes.

Approximately 0.05 gram $TiO_2$ (Ti-Pure 902+ available from DuPont) is next added to the open vial as well as 0.05 grams of GL0179B6/45 space beads available from MO-SCI Specialty Products, Rolla, Mo. 65401 USA, and then mixed using a Vortex mixer.

After mixing, the closed vial is put in an ultrasonic bath for approximately 50 minutes. Care is taken to avoid temperatures over 40° C. while the sample is in the ultrasonic bath. The sample is stored in the dark until used to make a combined formulation with long wavelength semiconductor and additional matrix material.

D. Preparation of Optical Material & Layer Including Red and Orange Emitting Semiconductor Nanocrystals:

An optical material is formed by adding together in a 20 ml vial, 2.52 grams of the host material including spacer beads (prepared substantially in accordance with the procedure described in Example 6C), 0.99 grams of the optical material of Example 6B and 1.01 grams of the optical material of Example 6A. The mixture was stirred using a Vortex mixer followed by sonification in an ultrasonic bath for approximately 50 minutes.

Sample material from the combination vial is dispensed onto a Hexagon shaped flat Borosilicate glass which was previously cleaned using a caustic base bath, acid rinse, deionized water rinse, and a methanol wipe. A second Hexagon plate of the same size also previously cleaned is placed on top of the dispensed sample material and the sandwiched structure is massaged to spread the formulation evenly between the two glass plates. Excess formulation which squeezed out of the structure is wiped off of the outer portion of the glass and the Hexagon sandwich is cured in a 5000-EC UV Light Curing Flood Lamp from DYMAX Corporation system with an H-bulb (225 mW/cm$^2$) for 10 seconds. The thickness of the nanocrystal containing layer is comprises approximately 70-79 μm (approximately 360 mg of formulation).

The Hexagon sandwich consisting of two Hexagon shaped flat plates of Borosilicate glass with cured layer of acrylic containing a sample of the optical material prepared substantially as described in Example 6.

Six samples (Samples A-F) were prepared substantially as described above in Example 5. Initial CCT, CRI, and External Quantum Efficiency measurements were taken for each sample prior to heating each sample to approximately 50° C. and irradiating the sample with approximately 30 mW/cm2 of 450 nm blue light for the time specified in following Table 3 for each of the samples. CCT, CRI, and EQE measurements were taken after the irradiation time listed for the respective sample. The data is set forth in the following Table 3.

TABLE 3

| | | | | | | | |
|---|---|---|---|---|---|---|---|
| Irradiation at 50° C. @ 30 mW/cm2 | | | | | | | |
| Sample Label | Initial CCT (K) | Initial CRI | Initial EQE (%) | Irradiation Time, Hrs | Final CCT (K) | Final CRI | Final EQE (%) |
| A | 2649 | 86.5 | 62 | 1 | 2482 | 87.1 | 78 |
| B | 2664 | 85.6 | — | 13 | 2519 | 87 | 82 |
| C | 2609 | 85.6 | 65 | 2 | 2444 | 87.1 | 77 |
| D | 2641 | 85.4 | 62 | 10* | 2472 | 87.2 | 80 |
| E | 2659 | 85.2 | 63 | 11 | 2480 | 87.3 | 80 |
| F | 2684 | 84.5 | 60 | 11 | 2446 | 87.3 | 80 |

*2 hrs 50 C. @ 30 mW/cm2 450 nm, 8 hrs 50 C. @ 15 mW/cm2 450 nm

Additional information useful with the present invention relating to optical components, color conversion materials, and lighting systems, lamps, and other lighting components is found in International Application No. PCT/US2009/02789, filed 6 May 2009, of QD Vision, Inc., et al, which is hereby incorporated herein by reference in its entirety.

In certain embodiments, a desired ligand can be attached to a semiconductor nanocrystal by building the desired functionality into the phosphonic acid derivative.

Following is a non-limiting example of a schematic of a general synthetic procedure for generating a desired phosphonic acid derivative:

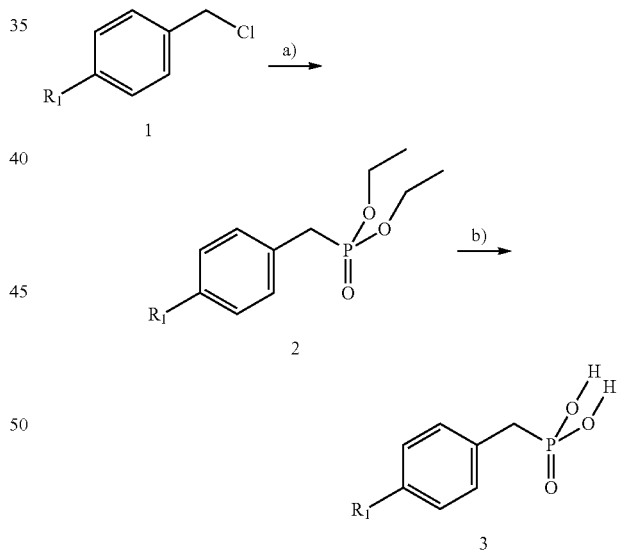

a) NaH, THF, NaI, P(OEt)$_3$ and 1.
b) 1. TMSBr, CH$_2$Cl$_2$. 2. H$_2$O.

Also refer to *The Chemistry of Organophosphorus Compounds, Volume 4: Ter-and Quinque-Valent Phosphorus Acids and Their Derivatives*, Frank R. Hartley (Editor), April 1996 for more general synthetic procedures for generating phosphonic acid derivatives.

In certain embodiments, a desired ligand can be attached to a semiconductor nanocrystal by building the desired functionality into, e.g., a phosphonic acid derivative, an amine derivative, or both.

Following is a non-limiting example of a schematic of a general synthetic procedure for generating a desired amine derivative:

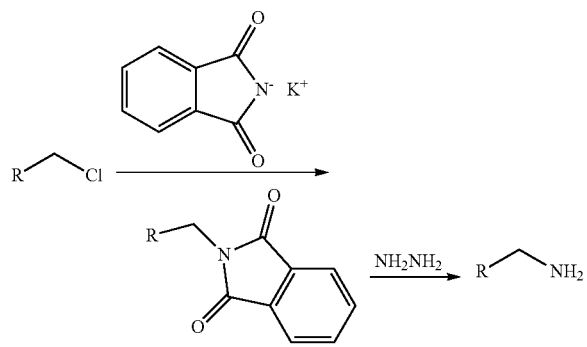

Nanoparticles can have various shapes, including, but not limited to, sphere, rod, disk, other shapes, and mixtures of various shaped particles.

Narrow size distribution, high quality semiconductor nanocrystals with high fluorescence efficiency can be prepared using previously established literature procedures and used as the building blocks. See, C. B. Murray et al., J. Amer. Chem. Soc. 1993, 115, 8706, B. O. Dabbousi et al., J. Phys. Chem. B 1997, 101, 9463, each of which is incorporated by reference in its entirety. Other methods known or readily ascertainable by the skilled artisan can also be used.

In certain embodiments, nanoparticles comprise chemically synthesized colloidal nanoparticles (nanoparticles), such as semiconductor nanocrystals or quantum dots. In certain preferred embodiments, the nanoparticles (e.g., semiconductor nanocrystals) have a diameter in a range from about 1 to about 10 nm. In certain embodiments, at least a portion of the nanoparticles, and preferably all of the nanoparticles, include one or more ligands attached to a surface of a nanoparticle. See, C. B. Murray et al., Annu. Rev. Mat. Sci., 30, 545-610 (2000), which is incorporated in its entirety. These zero-dimensional structures show strong quantum confinement effects that can be harnessed in designing bottom-up chemical approaches to create complex heterostructures with electronic and optical properties that are tunable with the size of the nanocrystals.

Light-emissive nanoparticles can confine electrons and holes and have a photoluminescent property to absorb light and re-emit different wavelength light. Color characteristics of emitted light from light-emissive nanoparticles depend on the size and chemical composition of the nanoparticles.

In certain embodiments, light-emissive nanoparticles include at least one type of light-emissive nanoparticle with respect to chemical composition and size. The type(s) of light-emissive nanoparticles included in various aspects or embodiments of the inventions contemplated by this disclosure are determined by the wavelength of light to be converted and the wavelengths of the desired light output. In certain embodiments, two or more types of light-emissive nanoparticles can be used that emit light at the same or different wavelengths.

Emission from semiconductor nanocrystals can occur at an emission wavelength when one or more of the nanocrystals is excited. The emission has a frequency that corresponds to the band gap of the quantum confined semiconductor material. The band gap is a function of the size of the nanocrystal. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases.

The emission from a nanocrystal can be a narrow Gaussian emission band that can be tuned through the complete wavelength range of the ultraviolet, visible, or infrared regions of the spectrum by varying the size of the nanocrystal, the composition of the nanocrystal, or both. The narrow size distribution of a population of nanocrystals can result in emission of light in a narrow spectral range. The population can be monodisperse and can exhibit less than a 15% rms deviation in diameter of the nanocrystals, preferably less than 10%, more preferably less than 5%. Spectral emissions in a narrow range of no greater than about 75 nm, preferably 60 nm, more preferably 40 nm, and most preferably 30 nm full width at half max (FWHM) can be observed. The breadth of the emission decreases as the dispersity of nanocrystal diameters decreases.

Semiconductor nanocrystals can have high emission quantum efficiencies such as greater than 10%, 20%, 30%, 40%, 50%, 60%, 70%, or 80%. The semiconductor forming the nanocrystals can include Group IV elements, Group II-VI compounds, Group II-V compounds, Group III-VI compounds, Group III-V compounds, Group IV-VI compounds, Group I-III-VI compounds, Group II-IV-VI compounds, or Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

Examples of methods of preparing monodisperse semiconductor nanocrystals include pyrolysis of organometallic reagents, such as dimethyl cadmium, injected into a hot, coordinating solvent. This permits discrete nucleation and results in the controlled growth of macroscopic quantities of nanocrystals. Preparation and manipulation of nanocrystals are described, for example, in U.S. Pat. No. 6,322,901, which is incorporated herein by reference in its entirety. Such methods of manufacturing nanocrystals involve a colloidal growth process. Colloidal growth occurs by rapidly injecting an M donor and an X donor into a hot coordinating solvent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M donor or X donor, the growth period can be shortened.

The M donor can be an inorganic compound, an organometallic compound, or elemental metal. For example, M can be cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis(silyl)chalcogenide, dioxygen, an ammonium salt, or a tris(silyl)pnictide. Suitable X donors include dioxygen, bis(trimethylsilyl)selenide ((TMS)$_2$Se), trialkyl phosphine selenides such as (tri-n-octylphosphine)selenide (TOPSe) or (tri-n-butylphosphine)selenide (TBPSe), trialkyl phosphine tellurides such as (tri-n-octylphosphine) telluride (TOPTe) or hexapropylphosphorustriamide telluride (HPPTTe), bis(trimethylsilyl)telluride ((TMS)$_2$Te), bis(trimethylsilyl)sulfide ((TMS)$_2$S), a trialkyl phosphine sulfide such as (tri-n-octylphosphine) sulfide (TOPS), an ammonium salt such as an ammonium halide (e.g., NH$_4$Cl), tris(trimethylsilyl)phosphide ((TMS)$_3$P), tris(trimethylsilyl)arsenide ((TMS)$_3$As), or tris(trimethylsilyl)antimonide ((TMS)$_3$Sb). In certain embodiments, the M donor and the X donor can be moieties within the same molecule.

A coordinating solvent can help control the growth of nanocrystals. The coordinating solvent is a compound having a donor lone pair that, for example, has a lone electron pair available to coordinate to a surface of the growing nanocrystal. Solvent coordination can stabilize the growing nanocrystal. Typical coordinating solvents include alkyl phosphines, alkyl phosphine oxides, alkyl phosphonic acids, or alkyl phosphinic acids, however, other coordinating solvents, such as pyridines, furans, and amines may also be suitable for the nanocrystal production. Examples of suitable coordinating solvents include, but are not limited to, pyridine, tri-n-octyl phosphine (TOP), tri-n-octyl phosphine oxide (TOPO) and tris-hydroxylpropylphosphine (tHPP). Technical grade TOPO can be used.

In certain methods, a non-coordinating or weakly coordinating solvent can be used.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter and choosing the proper composition of the semiconducting material, the emission spectra of the nanocrystals can be tuned continuously over the wavelength range of 300 nm to 5 microns.

Semiconductor nanocrystals include, for example, inorganic crystallites between about 1 nm and about 1000 nm in diameter, preferably between about 2 nm and about 50 um, more preferably about 1 nm to about 20 nm (such as about 6, 7, 8, 9, 10, 11, 12, 13, 14, 15, 16, 17, 18, 19, or 20 nm).

A semiconductor nanocrystal typically has a diameter of less than 150 Å. A population of nanocrystals preferably has average diameters in the range of 15 Å to 125 Å.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M comprises one or more metals (e.g., but not limited to, cadmium, zinc, magnesium, mercury, aluminum, gallium, indium, thallium, or mixtures thereof), and X comprises one or more members of Group IV, V, or VI (e.g., but not limited to, oxygen, sulfur, selenium, tellurium, nitrogen, phosphorus, arsenic, antimony, or mixtures thereof). In certain embodiments, a nanocrystal can comprise a Group II-VI compound, Group II-V compound, Group III-VI compound, Group III-V compound, Group IV-VI compound, Group I-III-VI compound, Group II-IV-VI compound, and Group II-IV-V compound. In certain embodiments, a nanocrystal can comprise a Group IV element.

The core can have an overcoating on a surface of the core. The overcoating can be a semiconductor material having a composition different from the composition of the core. The overcoat of a semiconductor material on a surface of the nanocrystal can include a Group II-VI compound, Group II-V compound, Group III-VI compound, Group III-V compound, Group IV-VI compound, Group I-III-VI compound, Group II-IV-VI compound, and Group II-IV-V compound, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. In certain embodiments, a nanocrystal can comprise a Group IV element.

For example, ZnS, ZnSe or CdS overcoatings can be grown on CdSe or CdTe nanocrystals. An overcoating process is described, for example, in U.S. Pat. No. 6,322,901. By adjusting the temperature of the reaction mixture during overcoating and monitoring the absorption spectrum of the core, over coated materials having high emission quantum efficiencies and narrow size distributions can be obtained.

The particle size distribution can be further refined by size selective precipitation with a poor solvent for the nanocrystals, such as methanol/butanol as described in U.S. Pat. No. 6,322,901. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

Transmission electron microscopy (TEM) can provide information about the size, shape, and distribution of the nanocrystal population. Powder x-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from x-ray diffraction data using, for example, the Scherrer equation. It also can be estimated from the UVNis absorption spectrum.

Narrow FWHM of nanocrystals can result in saturated color emission. This can lead to efficient nanocrystal-light emitting devices even in the red and blue parts of the spectrum, since in nanocrystal emitting devices no photons are lost to infrared and UV emission. The broadly tunable, saturated color emission over the entire visible spectrum of a single material system is unmatched by any class of organic chromophores. Furthermore, environmental stability of covalently bonded inorganic nanocrystals suggests that device lifetimes of hybrid organic/inorganic light emitting devices should match or exceed that of all-organic light emitting devices, when nanocrystals are used as luminescent centers. The degeneracy of the band edge energy levels of nanocrystals facilitates capture and radiative recombination of all possible excitons, whether generated by direct charge injection or energy transfer. The maximum theoretical nanocrystal-light emitting device efficiencies are therefore comparable to the unity efficiency of phosphorescent organic light emitting devices. The nanocrystal's excited state lifetime ($\tau$) is much shorter ($\tau \approx 10$ ns) than a typical phosphor ($\tau > 0.5$ μs), enabling nanocrystal-light emitting devices to operate efficiently even at high current density.

Nanoparticles in accordance with the present inventions can be included in emissive materials for use in light-emitting devices, displays, and other optoelectronic and electronic devices, which are well-known. Examples also include, but not limited to, those described, for example, in International Application No. PCT/US2007/013152, entitled "Light-Emitting Devices And Displays With Improved Performance", of QD Vision, Inc., et al., filed 4 Jun. 2007, and in International Application No, PCT/US2009/002123, entitled "Light-Emitting Device Including Quantum Dots", of QD Vision, Inc., et al., filed 3 Apr. 2009, International Application No. US2009/02789, entitled "Solid State Lighting Devices Including Quantum Confined Semiconductor Nanoparticles, An Optical Component For A Solid State Light Device, And Methods", of QD Vision, Inc., et al., filed 6 May 2009, and International Application No. PCT/US2009/002796, entitled "Optical Components, Systems Including An Optical Component, and Devices", of QD Vision, Inc., et al., filed 6 May 2009, each of the foregoing being hereby incorporated herein by reference in its entirety.

Nanoparticles in accordance with the present inventions can be included in photoluminescent applications including, but not limited to, those described in International Application No. PCT/US2008/007902, entitled "Compositions, Optical Component, System Including An Optical Component, Devices, And Other Products", of QD Vision, Inc., et al., filed 25 Jun. 2008. Each of the foregoing are hereby incorporated herein by reference in its entirety.

Other materials, techniques, methods, applications, and information that may be useful with the present invention are described in International Patent Application No. PCT/US2007/024750, entitled "Improved Composites And Devices Including Nanoparticles", of Coe-Sullivan, et al, filed 3 Dec. 2007, U.S. Application No. 61/083,998, entitled "Functionalized Nanoparticles And Method", of Breen et al., filed 28 Jul. 2008, International Application No. PCT/US2008/010651, entitled "Functionalized Nanoparticles And Method", of Breen et al., filed 12 Sep. 2008, and International Application No. PCT/US2007/014711, entitled "Methods For Depositing Nanomaterial, Methods For Fabricating A Device, And Methods For Fabricating An Array Of Devices", of QD Vision, Inc. et al., filed 25 Jun. 2007; each of the foregoing being hereby incorporated herein by reference in its entirety.

As used herein, the singular forms "a", "an" and "the" include plural unless the context clearly dictates otherwise. Thus, for example, reference to an emissive material includes reference to one or more of such materials.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The terms and expressions which, have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. Additional embodiments of the present invention will also be apparent to those skilled in the art from consideration of the specification and practice of the invention disclosed herein. It is intended that the specification and examples be considered as exemplary only, with a true scope and spirit of the invention being indicated by the following claims and equivalents thereof.

All patents, patent applications, and publications mentioned above are herein incorporated by reference in their entirety for all purposes. None of the patents, patent applications, and publications mentioned herein are admitted to be prior art.

The invention claimed is:

1. A nanoparticle including a ligand attached to a surface thereof, wherein the ligand is represented by the formula:

X-Sp-Z wherein:

X represents: a secondary amine group, a urea, a thiourea, an amide group, a carboxylic acid or carboxylate group, a phosphonic acid group, an arsonic acid group, a phosphoric acid group, a phosphinic acid group, a phosphinate group, a phosphinite group, a phosphine group, an arsenic acid group, an arsenate group, an arsenous acid group, an arsenite group, an arsinic acid group, an arsine oxide group, or an arsine group;

Sp represents a group capable of allowing a transfer of charge or an insulating group; and Z represents a multifunctional group including three or more functional groups capable of communicating a specific property or chemical reactivity to the nanoparticle, wherein Z includes a cyclic group including two or more functional substituent groups, wherein the cyclic group and at least two functional substituent groups are chemically distinct and at least one of the groups included in Z is selected to facilitate colloidal dispersion of the nanoparticle in an apolar solvent, non-polar, and/or a low polarity solvent, and wherein Z is not reactive upon exposure to light, and wherein the ligand is a native ligand that attaches or coordinates to the nanoparticle surface during the growth or overcoating thereof with an overcoating material comprising a semiconductor material.

2. A nanoparticle in accordance with claim 1, wherein Z includes at least one functional group which can exhibit dispersion bonding characteristics, polar bonding characteristics, and/or hydrogen bonding characteristics.

3. A nanoparticle in accordance with claim 1, wherein Z includes a thiol, carboxyl, hydroxyl, amino, amine, sulfo, bifunctional group, and/or a polyfunctional group.

4. A nanoparticle in accordance with claim 1, wherein Z includes a polar group.

5. A nanoparticle in accordance with claim 1, wherein at least one functional group included in Z is selected to facilitate a colloidal dispersion of the nanoparticle in a specific solvent defined by a given polarity.

6. A nanoparticle in accordance with claim 1, wherein Z includes a functional group comprising a polar group, a halogen group, an aliphatic group, an aromatic group, or mixtures of three or more thereof.

7. A nanoparticle in accordance with claim 1, wherein Z includes functional groups selected to not render the nanoparticle dispersible in a liquid medium that includes water.

8. A nanoparticle in accordance with claim 1, wherein two or more identical or different Z groups are further present on the same ligand.

9. A nanoparticle in accordance with claim 1, the nanoparticle includes two or more chemically distinct ligands attached to a surface thereof, at least two of said ligands being represented by the formula:

X-Sp-Z.

10. A nanoparticle in accordance with claim 9, wherein the at least two of the ligands represented by the formula X-Sp-Z are chemically distinct.

11. A nanoparticle in accordance with claim 9, wherein a first ligand is represented by the formula:

N-Sp-Z wherein N represents a primary amine group, a secondary amine group, an imidizole group, an amide group; and
a second ligand is represented by the formula:

Y-Sp-Z wherein Y represents a carboxylic acid group, a carboxylate group, a phosphonic acid group, an arsonic acid group, a phosphoric acid group, a phosphinic acid group, a phosphinate group, a phosphinite group, a phosphine group, an arsenic acid group, an arsenate group, an arsenous acid group, an arsenite group, an arsinic acid group, an arsine oxide group, or an arsine group.

12. A nanoparticle in accordance with claim 1, wherein the nanoparticle possesses photoluminescent properties.

13. A nanoparticle in accordance with claim 1, wherein the nanoparticle comprises a semiconductor nanocrystal.

14. A nanoparticle in accordance with claim 1, wherein the nanoparticle comprises a semiconductor nanocrystal including a core comprising a first semiconductor material and a shell disposed over at least a portion of a surface of the core, the shell comprising a second semiconductor material.

15. A nanoparticle including a ligand attached to a surface thereof, wherein the ligand is represented by the formula:

X-Sp-Z wherein:
X represents: a secondary amine group, a urea, a thiourea, an amide group, a carboxylic acid or carboxylate group, a phosphonic acid group, an arsonic acid group, a phosphoric acid group, a phosphinic acid group, a phosphinate group, a phosphinite group, a phosphine group, an arsenic acid group, an arsenate group, an arsenous acid group, an arsenite group, an arsinic acid group, an arsine oxide group, or an arsine group;
Sp represents a group capable of allowing a transfer of charge or an insulating group; and
Z represents a multifunctional group including three or more functional groups capable of communicating a specific property or chemical reactivity to the nanoparticle, wherein Z includes a cyclic group including two or more functional substituent groups, wherein the cyclic group and at least two functional substituent groups are chemically distinct, wherein Z is not reactive upon exposure to light, and wherein Z includes a halogenated group, wherein the ligand is a native ligand that attaches or coordinates to the nanoparticle surface during the growth or overcoating thereof with an overcoating material comprising a semiconductor material.

16. A nanoparticle in accordance with claim 1, wherein the ligand coordinates with the nanoparticle surface via the X group.

17. A nanoparticle in accordance with claim 1 wherein the cyclic group comprises a saturated or unsaturated cyclic compound, a saturated or unsaturated cyclic compound that includes at least one heteroatom, an aromatic compound, or an aromatic compound that includes at least one hetero-atom.

18. A nanoparticle in accordance with claim 15 wherein the cyclic group comprises a saturated or unsaturated cyclic compound, a saturated or unsaturated cyclic compound that includes at least one heteroatom, an aromatic compound, or an aromatic compound that includes at least one hetero-atom.

19. A nanoparticle in accordance with claim 1 wherein X represents a phosphonic acid group.

20. A nanoparticle in accordance with claim 15 wherein X represents a phosphonic acid group.

* * * * *